(12) United States Patent
Jajal et al.

(10) Patent No.: US 11,129,679 B2
(45) Date of Patent: Sep. 28, 2021

(54) FIBER OPTIC TRACKING SYSTEM

(71) Applicant: MAKO Surgical Corp., Ft. Lauderdale, FL (US)

(72) Inventors: Ketan Jajal, Gujarat (IN); Justin Gerges, Waldwick, NJ (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 745 days.

(21) Appl. No.: 15/812,657

(22) Filed: Nov. 14, 2017

(65) Prior Publication Data

US 2019/0142522 A1  May 16, 2019

(51) Int. Cl.
*A61B 34/20* (2016.01)
*A61B 34/00* (2016.01)
*A61B 17/34* (2006.01)

(52) U.S. Cl.
CPC .......... *A61B 34/20* (2016.02); *A61B 17/3423* (2013.01); *A61B 34/25* (2016.02);
(Continued)

(58) Field of Classification Search
CPC ........ A61B 2034/2061; A61B 17/3423; A61B 2017/3429; A61B 34/20; A61B 2034/2055; A61B 2034/2051; A61B 2034/2068; A61B 2090/306; A61B 2090/3945; A61B 2090/3937; A61B 5/1076; G01B 11/165; G01B 11/18; G02B 6/02042;
(Continued)

(56) References Cited

U.S. PATENT DOCUMENTS 5,073,402 A  12/1991  Henderson
5,335,663 A   8/1994  Oakley et al.
(Continued)

FOREIGN PATENT DOCUMENTS

EP  0 391 558  10/1990
EP  0 416 931   3/1991
(Continued)

OTHER PUBLICATIONS

The three dimensions (https://www.ck12.org/geometry/geometric-definitions/lesson/The-Three-Dimensions-GEOM-HNRS/, retrieved Dec. 9, 2020).*
(Continued)

*Primary Examiner* — Carolyn A Pehlke
(74) *Attorney, Agent, or Firm* — Foley & Lardner LLP

(57) ABSTRACT

A fiber optic tracking system includes a light source, a first optical fiber, a second optical fiber, a sensing unit, and a controller operatively coupled to the sensing unit. Each optical fiber includes a plurality of sensing sections and has a fixed sensing point located along its respective length that is fixed relative to tissue. Each optical fiber is configured to receive an optical signal from the light source. The sensing sections are configured to modify the optical signals in response to a deformation of the respective optical fiber. The sensing unit is configured to receive modified optical signals from the first optical fiber and the second optical fiber. The controller is configured to determine locations in a working coordinate system of the fixed sensing points using the modified optical signals and determine a pose of the tissue based on the locations of the fixed sensing points.

21 Claims, 19 Drawing Sheets

(52) U.S. Cl.
CPC ............... *A61B 2034/2055* (2016.02); *A61B 2034/2061* (2016.02)

(58) Field of Classification Search
CPC ... G02B 6/02057; G02B 6/022; A61F 2/4657; G01D 5/35316
See application file for complete search history.

(56) References Cited

U.S. PATENT DOCUMENTS

| | | | |
|---|---|---|---|
| 5,374,821 | A | 12/1994 | Muhs et al. |
| 5,437,283 | A | 8/1995 | Ranalletta et al. |
| 5,469,853 | A | 11/1995 | Law et al. |
| 5,919,140 | A | 7/1999 | Perelman et al. |
| 6,138,046 | A | 10/2000 | Dalton |
| 6,256,090 | B1 | 7/2001 | Chen et al. |
| 6,321,111 | B1 | 11/2001 | Perelman et al. |
| 6,466,713 | B2 | 10/2002 | Everett et al. |
| 6,514,277 | B1 | 2/2003 | Lilge et al. |
| 6,564,087 | B1 | 5/2003 | Pitris et al. |
| 7,435,219 | B2 | 10/2008 | Kim |
| 7,720,322 | B2 | 5/2010 | Prisco |
| 7,772,541 | B2* | 8/2010 | Froggatt ............... G01D 5/3539 250/227.23 |
| 7,837,634 | B2 | 11/2010 | Costello |
| 7,945,312 | B2 | 5/2011 | Hular et al. |
| 7,992,573 | B2 | 8/2011 | Wilson et al. |
| 8,355,134 | B2 | 1/2013 | Chau et al. |
| 8,623,028 | B2 | 1/2014 | Rogers et al. |
| 8,882,662 | B2 | 11/2014 | Charles |
| 8,936,630 | B2 | 1/2015 | Denison et al. |
| 8,986,358 | B2 | 3/2015 | Svanberg et al. |
| 9,044,179 | B2 | 6/2015 | Wilson et al. |
| 9,050,131 | B2 | 6/2015 | Van Vorhis et al. |
| 9,179,985 | B2 | 11/2015 | Hendriks et al. |
| 9,216,068 | B2 | 12/2015 | Tesar |
| 10,603,047 | B2 | 3/2020 | Ding et al. |
| 2002/0021866 | A1 | 2/2002 | Everett et al. |
| 2002/0183594 | A1* | 12/2002 | Beane ................. A61B 17/0293 600/207 |
| 2003/0045798 | A1 | 3/2003 | Hular et al. |
| 2005/0090717 | A1* | 4/2005 | Bonadio ................. A61B 1/32 600/208 |
| 2005/0203383 | A1* | 9/2005 | Moctezuma de la Barrera .......... A61B 8/58 600/424 |
| 2005/0215866 | A1 | 9/2005 | Kim |
| 2005/0261568 | A1 | 11/2005 | Hular et al. |
| 2006/0036164 | A1 | 2/2006 | Wilson et al. |
| 2006/0217793 | A1 | 9/2006 | Costello |
| 2008/0009749 | A1 | 1/2008 | Delianides et al. |
| 2008/0021283 | A1 | 1/2008 | Kuranda |
| 2008/0039715 | A1 | 2/2008 | Wilson et al. |
| 2008/0255461 | A1 | 10/2008 | Weersink et al. |
| 2008/0306391 | A1 | 12/2008 | Hular et al. |
| 2009/0018401 | A1 | 1/2009 | Kim |
| 2009/0182225 | A1 | 7/2009 | Foley et al. |
| 2009/0216097 | A1 | 8/2009 | Wilson et al. |
| 2009/0314925 | A1 | 12/2009 | Van Vorhis et al. |
| 2010/0317964 | A1 | 12/2010 | Hendriks et al. |
| 2011/0034971 | A1 | 2/2011 | Svanberg et al. |
| 2011/0069316 | A1 | 3/2011 | Chau et al. |
| 2011/0071473 | A1 | 3/2011 | Rogers et al. |
| 2011/0105869 | A1 | 5/2011 | Wilson et al. |
| 2011/0112435 | A1 | 5/2011 | Ramanujam et al. |
| 2011/0125077 | A1 | 5/2011 | Denison et al. |
| 2011/0125078 | A1 | 5/2011 | Denison et al. |
| 2011/0212411 | A1 | 9/2011 | Sinofsky |
| 2012/0065482 | A1 | 3/2012 | Robinson et al. |
| 2012/0289816 | A1 | 11/2012 | Mark et al. |
| 2013/0197373 | A1 | 8/2013 | Sharma et al. |
| 2014/0005484 | A1 | 1/2014 | Charles |
| 2014/0005485 | A1 | 1/2014 | Tesar et al. |
| 2014/0005486 | A1 | 1/2014 | Charles |
| 2014/0005487 | A1 | 1/2014 | Tesar |
| 2014/0005488 | A1 | 1/2014 | Charles et al. |
| 2014/0005489 | A1 | 1/2014 | Charles |
| 2014/0005555 | A1 | 1/2014 | Tesar |
| 2014/0066717 | A1 | 3/2014 | Rogers et al. |
| 2014/0114168 | A1 | 4/2014 | Block et al. |
| 2014/0276943 | A1* | 9/2014 | Bowling ............... A61B 90/03 606/130 |
| 2015/0018622 | A1 | 1/2015 | Tesar et al. |
| 2015/0057724 | A1 | 2/2015 | Kuhn et al. |
| 2015/0141759 | A1 | 5/2015 | Charles et al. |
| 2015/0209527 | A1 | 7/2015 | Kang et al. |
| 2015/0238073 | A1 | 8/2015 | Charles et al. |
| 2015/0272694 | A1 | 10/2015 | Charles |
| 2015/0359525 | A1 | 12/2015 | Hendriks et al. |
| 2015/0375006 | A1 | 12/2015 | Denison et al. |
| 2016/0100908 | A1 | 4/2016 | Tesar |
| 2016/0107003 | A1 | 4/2016 | Tsoref et al. |
| 2016/0113728 | A1 | 4/2016 | Piron et al. |
| 2016/0151116 | A1 | 6/2016 | Wayne et al. |
| 2016/0178357 | A1 | 6/2016 | Breisacher |
| 2016/0206384 | A1* | 7/2016 | Dimaio ............... A61B 17/1703 |
| 2016/0245990 | A1 | 8/2016 | Boyden et al. |
| 2016/0291313 | A1* | 10/2016 | Tojo ................... A61B 1/00165 |
| 2017/0202623 | A1* | 7/2017 | Richmond ........... G01B 11/165 |
| 2017/0281281 | A1* | 10/2017 | He ........................ A61B 34/20 |

FOREIGN PATENT DOCUMENTS

| | | |
|---|---|---|
| EP | 1 884 215 | 2/2008 |
| EP | 2 066 403 | 5/2010 |
| EP | 1 973 503 | 9/2013 |
| EP | 2 679 155 | 1/2014 |
| EP | 2 431 072 | 4/2014 |
| EP | 2 717 029 | 4/2014 |
| EP | 2 298 413 | 7/2015 |
| EP | 3 037 056 | 6/2016 |
| JP | 07-047081 | 2/1995 |
| JP | 2628355 | 7/1997 |
| JP | 11-178799 | 7/1999 |
| JP | 11-508352 | 7/1999 |
| JP | 3249820 | 1/2002 |
| JP | 2005-501586 | 1/2005 |
| JP | 2005-253983 | 9/2005 |
| JP | 2006-516739 | 7/2006 |
| JP | 2009-543607 | 12/2009 |
| JP | 2010-500140 | 1/2010 |
| JP | 2012-502714 | 2/2012 |
| JP | 2012-517252 | 8/2012 |
| JP | 5472987 | 4/2014 |
| JP | 2014-524303 | 9/2014 |
| JP | 2015-521913 | 8/2015 |
| JP | 2015-194506 | 11/2015 |
| JP | 2016-106890 | 6/2016 |
| WO | WO-94/13208 | 6/1994 |
| WO | WO-96/26431 | 8/1996 |
| WO | WO-00/42906 | 7/2000 |
| WO | WO-00/77491 | 12/2000 |
| WO | WO-01/85637 | 11/2001 |
| WO | WO-03/020119 | 3/2003 |
| WO | WO-2005/094695 | 10/2005 |
| WO | WO-2006/049787 | 5/2006 |
| WO | WO-2007/081811 | 7/2007 |
| WO | WO-2008/020050 | 2/2008 |
| WO | WO-2008/101201 | 8/2008 |
| WO | WO-2008/154533 | 12/2008 |
| WO | WO-2009/043045 | 4/2009 |
| WO | WO-2009/109879 | 9/2009 |
| WO | WO-2010/051463 | 5/2010 |
| WO | WO-2011/060054 | 5/2011 |
| WO | WO-2011/066320 | 6/2011 |
| WO | WO-2011/141918 | 11/2011 |
| WO | WO-2012/101584 | 8/2012 |
| WO | WO-2013057703 A1* | 4/2013 ............ A61B 5/6804 |
| WO | WO-2013/144830 | 10/2013 |
| WO | WO-2014/004717 | 1/2014 |
| WO | WO-2014/063163 | 4/2014 |
| WO | WO-2012/076631 | 9/2014 |
| WO | WO-2014/132110 | 9/2014 |
| WO | WO-2014/139023 | 9/2014 |

(56) References Cited

FOREIGN PATENT DOCUMENTS

| WO | WO-2014/189969 | 11/2014 |
| WO | WO-2015/038740 A1 | 3/2015 |
| WO | WO-2015/091521 | 6/2015 |
| WO | WO-2016/038489 | 3/2016 |
| WO | WO-2016/038499 | 3/2016 |
| WO | WO-2016/038531 | 3/2016 |
| WO | WO-2016/061431 | 4/2016 |
| WO | WO-2016/090047 | 7/2016 |
| WO | WO-2016/109877 | 7/2016 |
| WO | WO-2016/119039 | 8/2016 |
| WO | WO-2016/142738 | 9/2016 |

OTHER PUBLICATIONS

International Search Report and Written Opinion for International Application No. PCT/US2018/059449, dated May 15, 2019, 20 pages.
Partial International Search Report and Written Opinion and Invitation to Pay Additional Fees for International Application No. PCT/US2018/059449, dated Mar. 18, 2019, 15 pages.

\* cited by examiner

FIBER OPTIC TRACKING SYSTEM

BACKGROUND

The invention relates generally to fiber optic tracking, and more particularly to a fiber optic tracking system for tracking tissue or a surgical port and a method for fiber optic tracking of hard tissue or a surgical port.

It is often necessary to track the position of tissue during surgical procedures. Computer-assisted surgical systems have been developed that are commonly used to perform precise surgical tasks. These systems require accurate information throughout the duration of the procedure regarding the positions of tissue to operate properly.

Fiber optic systems have been developed to track objects in space. The optical fibers used in these systems include a number of sensing sections located along their lengths. One type of sensing section, called a fiber Bragg grating, reflects a certain wavelength of light depending in part upon the strain experienced by the optical fiber at the sensing section. By analyzing the reflected wavelengths, a three-dimensional model of the shape of the optical fiber may be generated. A system and method for determining the trajectory of an optical fiber are described in detail in European Patent Application Publication No. 3037056A1.

Conventional tracking systems used during surgical procedures are associated with a number of disadvantages that can include a failure to provide high accuracy and high sampling rate, and lacks an ability for robust tracking that is not easily affected by a surgical procedure or by surgical workflow. Fiber optic tracking systems are conventionally implemented using bone screws or other similar methods of coupling to hard tissue, which may be invasive.

In some procedures, surgical robots are utilized to perform certain tasks during surgery. Some of these tasks involve the use of surgical instruments inside an incision. Some of these surgical instruments are sharp and could inadvertently damage the soft tissue surrounding an incision if they come into contact with the soft tissue.

SUMMARY

In accordance with one aspect, the present disclosure is directed to a fiber optic tracking system for tracking tissue including a light source, a first optical fiber including a plurality of first sensing sections, a second optical fiber including a plurality of second sensing sections, a sensing unit, and a controller operatively coupled to the sensing unit. The first optical fiber has a first fixed sensing point located along a length of the first optical fiber that is fixed relative to tissue. The first optical fiber is configured to receive a first optical signal from the light source. The first sensing sections are configured to modify the first optical signal in response to a deformation of the first optical fiber. The second optical fiber has a second fixed sensing point located along a length of the second optical fiber that is fixed relative to the tissue. The second optical fiber is configured to receive a second optical signal from the light source. The second sensing sections are configured to modify the second optical signal in response to a deformation of the second optical fiber. The sensing unit is configured to receive modified optical signals from the first optical fiber and the second optical fiber. The controller is configured to determine locations in a working coordinate system of the first fixed sensing point and the second fixed sensing point using the modified optical signals and determine a pose of the tissue based on the locations of the first fixed sensing point and the second fixed sensing point.

According to another aspect, the present disclosure is directed to a fiber optic tracking system including a surgical port configured to be inserted into an incision, a light source, an optical fiber having a plurality of fixed sensing points located along a length of the optical fiber that are fixed relative to the surgical port, a sensing unit, and controller operatively coupled to the sensing unit. The optical fiber is configured to receive an optical signal from the light source. The optical fiber includes a plurality of sensing sections arranged along the length of the optical fiber and configured to modify the optical signal received by the optical fiber in response to a deformation of the optical fiber. The sensing unit is configured to receive a modified optical signal from the optical fiber. The controller is configured to determine locations in a working coordinate system of the fixed sensing points using the modified optical signal.

In accordance with yet another aspect, the present disclosure is directed to a method of tracking an incision including inserting a surgical port into the incision, providing a light source, and coupling an optical fiber to the surgical port such that a plurality of fixed sensing points along a length of the optical fiber are fixed relative to the surgical port. The optical fiber is configured to receive an optical signal from the light source. The optical fiber includes a plurality of sensing sections arranged along the length the optical fiber and configured to modify the optical signal received by the optical fiber in response to a deformation of the optical fiber. The method further includes receiving a modified optical signal from the optical fiber and determining locations in a working coordinate system of the fixed sensing points based on the modified optical signal.

It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments that, together with the description, serve to explain the principles and features of the present disclosure.

DETAILED DESCRIPTION

Reference will now be made in detail to exemplary embodiments of the present disclosure, examples of which are illustrated in the accompanying drawings.

Referring to the figures, systems for tracking the locations and/or orientations of incisions and/or rigid objects (e.g., hard tissue such as bones, surgical instruments, etc.) during surgery are shown and described. The systems described herein utilize shape sensing fiber optics to determine the locations of points in three-dimensional space corresponding to hard tissue or incisions. In some embodiments, one or more optical fibers are attached to hard tissue. In other embodiments, optical fibers are incorporated into a surgical port located inside an incision. The locations of the rigid objects and/or the incision may be provided to an operator or to a computer assisted surgery (CAS) system. The systems outlined herein provide accurate tracking without the need for large incisions or invasive pins traditionally used to mount vision trackers for navigated surgeries. Additionally, the optical fibers may eliminate the need for line of sight vision tracking.

Figure 1:
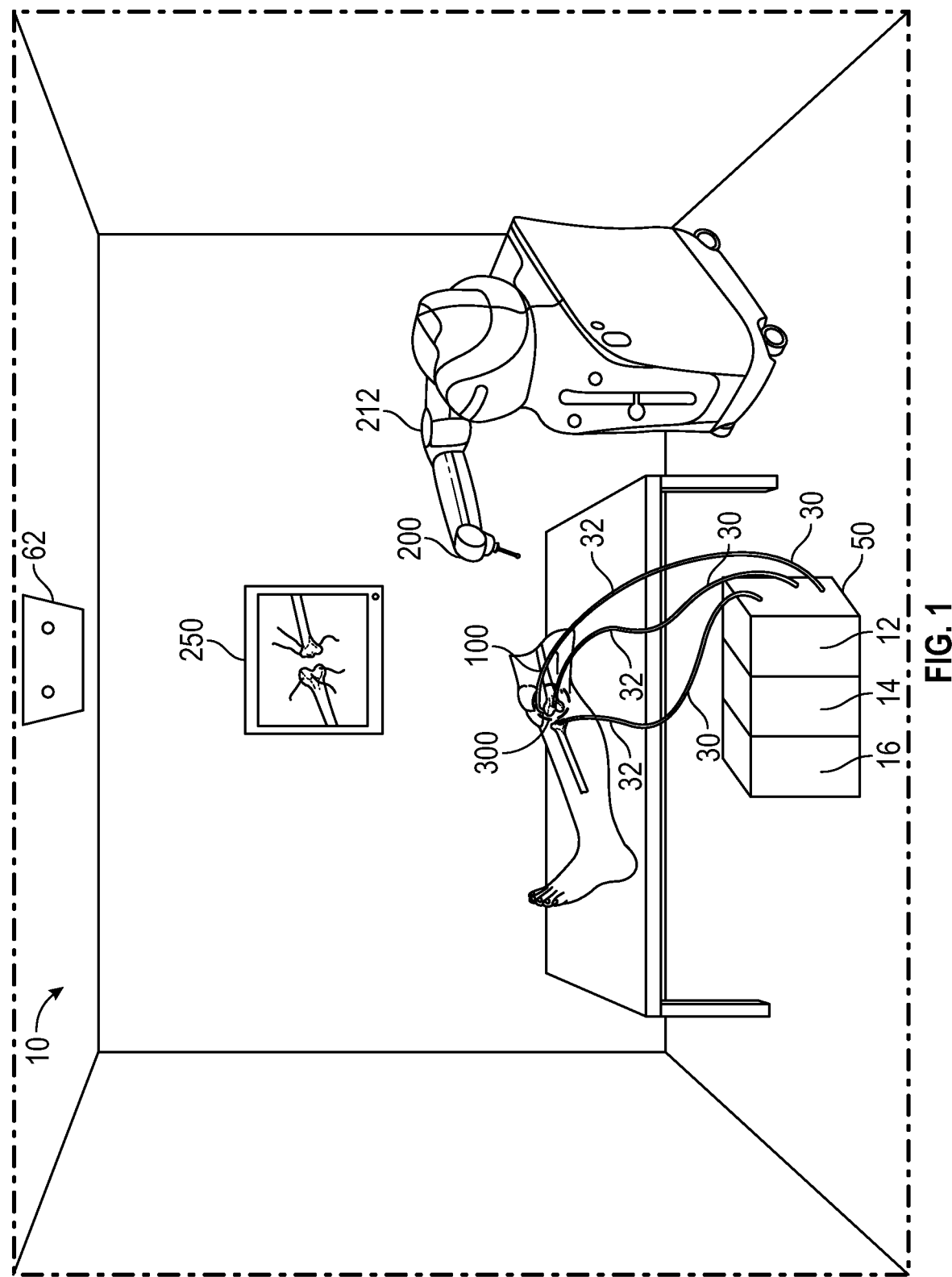
FIG. 1 provides a perspective view of an operating room in which a fiber optic tracking system is employed.

Referring to FIG. 1, a fiber optic tracking system 10 is shown according to an exemplary embodiment. The fiber optic tracking system includes a light source 12 configured to emit an optical signal (e.g., light), a sensing unit 14, and a controller 16 operatively coupled to the sensing unit 14. One or more optical fibers 30 are configured to receive the optical signal from the light source 12 and to each emit a modified optical signal that is received by the sensing unit 14. Each optical fiber 30 includes a number of sensing sections 32 along its length that modify the optical signal in response to a deformation of the optical fiber 30. The controller 16 is configured to use information from the sensing unit 14 regarding the modified optical signal to determine a shape of each optical fiber 30. The optical fibers 30 are coupled to an object (e.g., hard tissue or a surgical port), and the controller 16 tracks the object using information regarding the shapes each of the optical fibers 30. As used herein, tracking an object refers to determining the location, pose in six dimensions (i.e., the location and the orientation), and/or the shape of the object.

Figure 2:
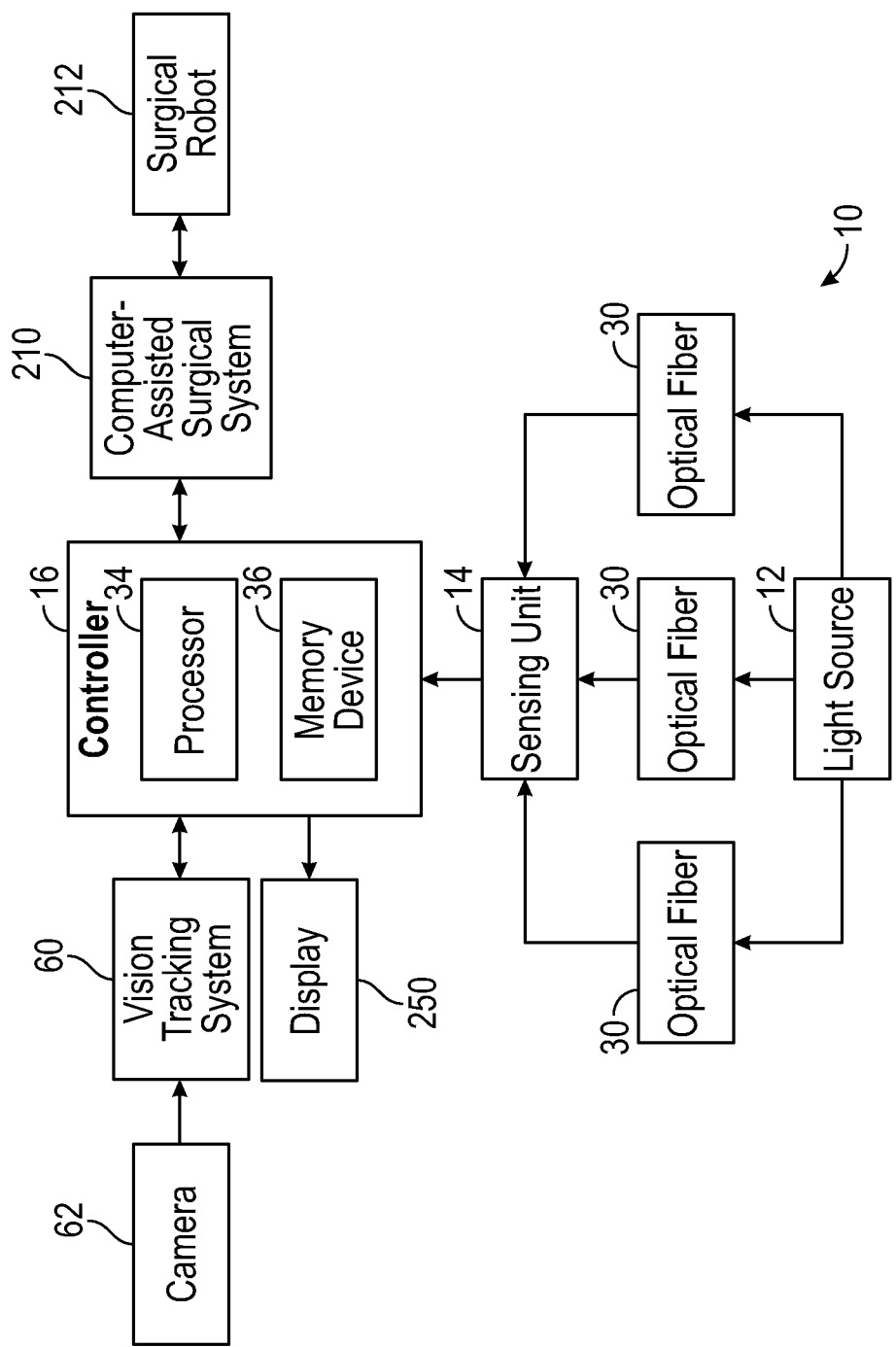
FIG. 2 provides a schematic illustration of a fiber optic tracking system.

Referring to FIG. 2, the light source 12 is shown in a block diagram of the fiber optic tracking system 10 according to an exemplary embodiment. The light source 12 is configured to emit an optical signal (e.g., light) into each of the optical fibers 30. In some embodiments, the light source 12 is coupled to an end of the optical fiber 30. In some embodiments, the light source 12 emits a specific band (i.e., a range of light wavelengths) or bands of optical signals. By way of example, the light source 12 may emit only light in the visible spectrum. The emitted band or bands may be modified by changing the type or operating parameters of the light source 12 or by applying an optical filter to an output of the light source 12. The light source 12 is preferably a broadband light source or a tunable laser (e.g., an ELED, LED, or SLD). In some embodiments, the light source 12 is operatively coupled to the controller 16 such that the controller 16 may vary the optical signal emitted from the light source 12. In other embodiments, the light source 12 is operatively decoupled from the controller 16. In some embodiments, the light source 12 emits a different optical signal into each of the optical fibers 30. In other embodiments, the light source 12 emits the same optical signal into each optical fiber 30.

Referring still to FIG. 2, the sensing unit 14 is shown. The sensing unit is configured to receive the modified optical signal from each optical fiber 30. In some embodiments, the sensing unit 14 is coupled to the same end of the optical fiber as the light source 12 (e.g., with an optical coupler), and the modified optical signal is reflected back to the sensing unit 14. The sensing unit can be configured to identify which modified optical signals come from the sensing sections 32. The sensing unit 14 may also compare the modified optical signal to the optical signal emitted by the light source 12. By way of example, the sensing unit 14 may be configured to determine which wavelengths of light are present in the modified optical signal and compare those wavelengths to the wavelengths present in the optical signal emitted by the light source 12. In some embodiments, the light source 12 and the sensing unit 14 are incorporated into the same device. The sensing unit 14 may comprise, for example, a conventional reflectometer, such as a frequency domain reflectometer. The sensing unit 14 is operatively coupled to the controller 16 such that the controller 16 receives information regarding the modified optical signal from the sensing unit 14. In some embodiments, some actions described herein as being performed by the sensing unit 14 are instead performed by the controller 16 and vice versa.

The fiber optic tracking system 10 includes a controller or processing circuit, shown as the controller 16. The controller 16 can include a processor 34 and memory device 36. Processor 34 can be implemented as a general purpose processor, an application specific integrated circuit (ASIC), one or more field programmable gate arrays (FPGAs), a group of processing components, or other suitable electronic processing components. Memory device 36 (e.g., memory, memory unit, storage device, etc.) is one or more devices (e.g., RAM, ROM, Flash memory, hard disk storage, etc.) for storing data and/or computer code for completing or facilitating the various processes, layers and modules described in the present application. Memory device 36 may be or include volatile memory or non-volatile memory. Memory device 36 may include database components, object code components, script components, or any other type of information structure for supporting the various activities and information structures described in the present application. According to an exemplary embodiment, memory device 36 is communicably connected to processor 34 via controller 16 and includes computer code for executing (e.g., by processing circuit and/or processor) one or more processes described herein.

The fiber optic tracking system 10 may further include a vision tracking system 60, camera 62, a display 250, a computer assisted surgical system 210 and a surgical robot 212, all of which are described herein.

Figure 3:
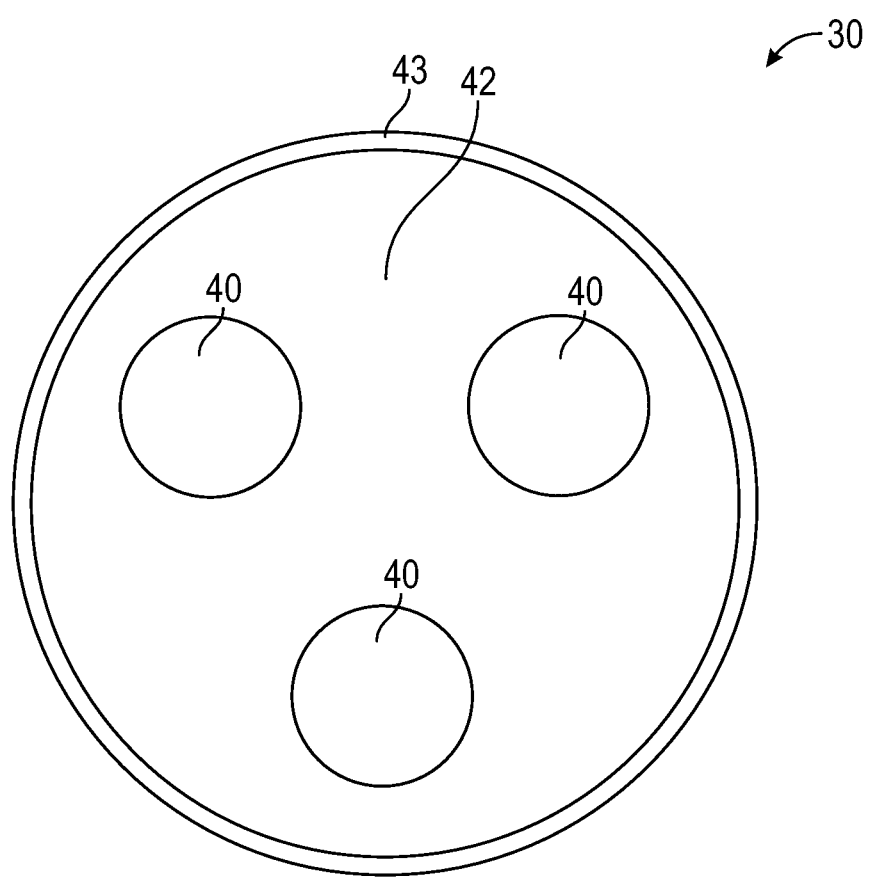
FIG. 3 provides a cross-sectional view of an exemplary optical fiber, in accordance with certain disclosed embodiments.
Figure 4A:
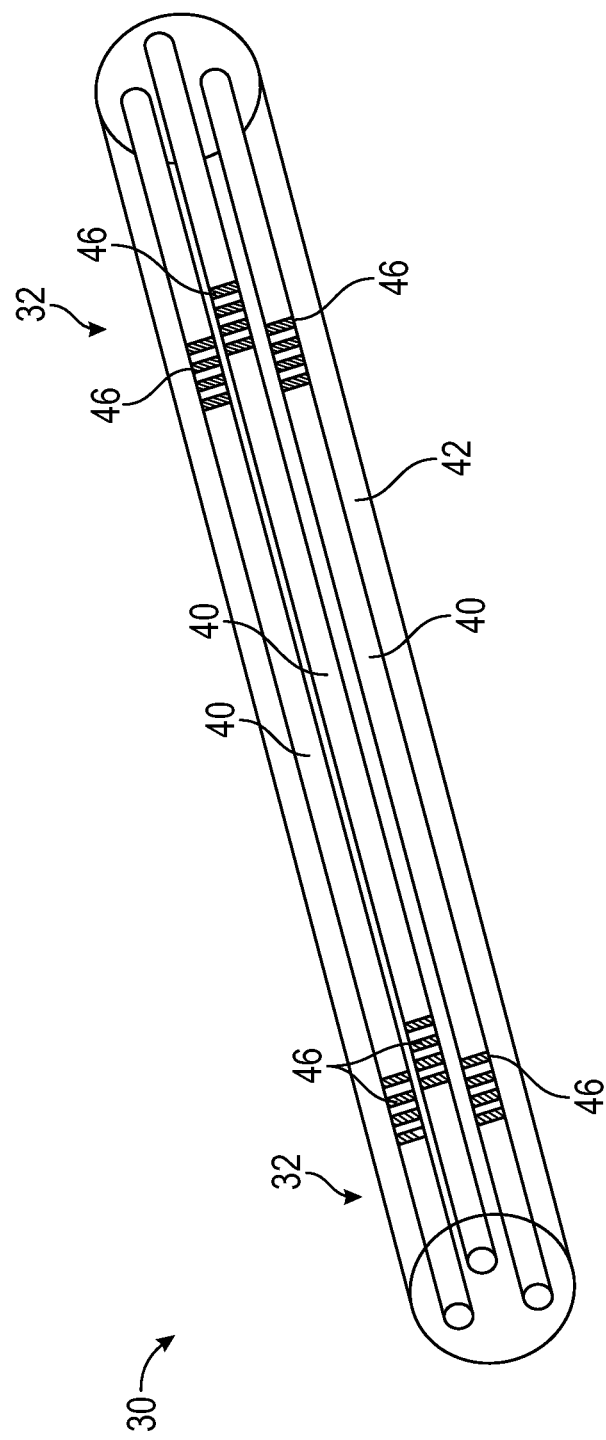
FIG. 4A provides a perspective view of an exemplary optical fiber, in accordance with certain disclosed embodiments.
Figure 4B:
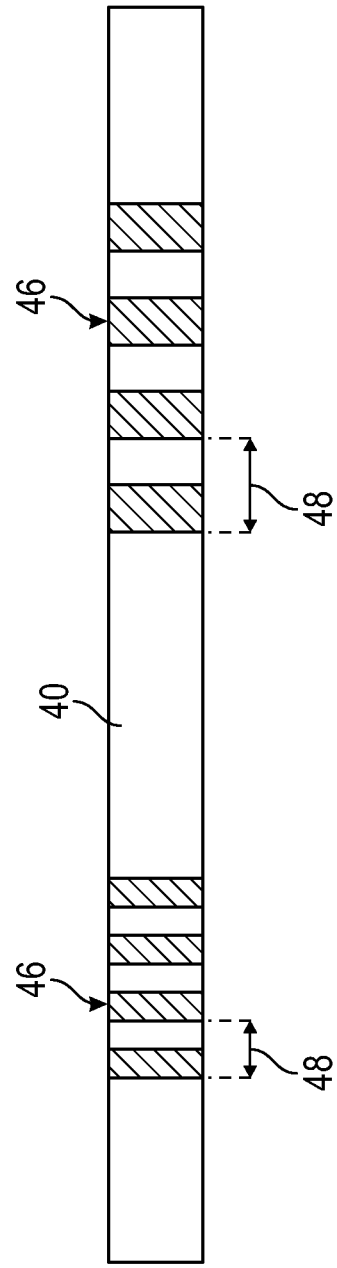
FIG. 4B provides a cross-sectional view of an exemplary core of an optical fiber, in accordance with the embodiment shown in FIG. 4A.

The optical fibers 30 are configured to receive an optical signal (e.g., visible light, ultraviolet light, etc.) from the light source 12 and guide the optical signal along a length of the optical fibers 30. Referring to FIGS. 3, 4A, and 4B, according to an exemplary embodiment, the optical fibers 30 each include one or more cores, shown as cores 40, along which the optical signal propagates. The cores 40 are made from a transparent material (e.g., glass) to allow the optical signal to travel along the length of the core 40. In some embodiments, each core 40 is surrounded by one or more outer layers. The outer layers may be or include one or more cladding layers having a refractive index selected to reduce or eliminate a leakage of the optical signal, strengthening layers to prevent breakage of the core 40, nonreactive layers to prevent reaction of the optical fiber 30 with the surrounding environment, protective layers to prevent damage to the interior of the optical fiber 30, or other types of layers. In the embodiment shown in FIG. 3, the optical fiber 30 is a tri-core fiber including three cores 40. The three cores 40 are all surrounded by a cladding outer layer 42, which is in turn surrounded by a protective outer layer 43. In other embodiments, the optical fiber 30 includes more or fewer than three cores 40. In some embodiments, the optical fiber 30 includes one or more single core optical fibers bundled together. In some embodiments, some or all of the length of the optical fiber 30 is flexible. In other embodiments, the optical fiber 30 includes a rigid portion 44 (e.g., the rigid portion 44 shown in FIG. 7A).

Referring to FIG. 4A, according to an exemplary embodiment, arranged along the length of the optical fiber 30 are the sensing sections 32. The sensing sections 32 are spaced apart from one another. In some embodiments, the sensing sections 32 are spaced a uniform distance apart from one another (e.g., 1 cm, 2 cm, 5 cm, etc.). In other embodiments, a distance between each sensing section 32 varies. Each sensing section 32 has a sensing component 46 associated with each core 40. In some embodiments, the sensing components 46 are located at the same points along each core 40 relative to one end of the optical fiber 30. By way of example, in the embodiment shown in FIG. 4A, each core 40 has a sensing component located in the same cross-sectional plane. In other embodiments, the sensing components 46 of one core 40 are staggered along the length of the core 40 relative to the sensing components 46 of another core 40.

The sensing components 46 modify the optical signal traveling through the core 40 with which each sensing component 46 is associated. In one embodiment, the sensing component 46 is a fiber Bragg grating. A fiber Bragg grating is a section of the core 40 along which the refractive index of the material of the core 40 changes repeatedly over a grating period 48, as illustrated in FIG. 4B depicting an exemplary embodiment. In FIG. 4B, the shaded and unshaded sections of the core 40 have different refractive indices. A fiber Bragg grating reflects a particular narrow band of light wavelengths, the wavelengths of this band being dependent in part upon the length of the grating period 48. A fiber Bragg grating can be created by periodically varying the refractive index of the core 40 using various methods, such as exposing the core 40 to ultraviolet light. In other embodiments, other types of sensing components 46 are used. The sensing components 46 produce modified optical signals based on strain or local bend of the core 40 or changes thereto (e.g., caused by deformation of the optical fiber 30). By way of example, as a fiber Bragg grating experiences strain, the band of reflected wavelengths shifts (e.g., changes in wavelength).

In some embodiments, the sensing components 46 in one fiber each return a distinct modified optical signal. By way of example, in an embodiment that incorporates fiber Bragg gratings, each sensing component 46 has a different grating period 48 such that the reflected wavelength band for each sensing component 46 is unique to that sensing component 46. The controller 16 may be configured to identify the portion of the modified optical signal associated with each sensing component 46 based on the wavelengths of the modified optical signal. The controller 16 may be configured to monitor the reflected wavelength band associated with each sensing component 46 for a shift in wavelength. The controller 16 may then utilize this shift in wavelength to determine the strain on the corresponding sensing component 46. Some sensing components 46 are sensitive to other environmental factors, such as temperature. In some embodiments, the controller 16 is configured to compensate for these factors when determining strain. By way of example, the controller 16 may be operatively coupled to a temperature sensor (e.g., that measures an ambient room temperature, that measures a temperature of a body into which the optical fiber 30 is inserted, etc.) and may be configured to modify the determined strain at each sensing component 46 by a temperature-dependent factor.

The determined strain at each sensing component 46 may be used to determine a shape of the optical fiber 30 using methods previously known in the art. The method selected is dependent on the number and arrangement of cores 40 and the type of sensing components 46 used, among other factors. In some cases, it may be advantageous to modify (e.g., decrease) the distance between the sensing sections 32 in order to increase the accuracy of the determined shape. The locations of each sensing section 32 along the length of the optical fiber 30 may be predetermined and stored in the memory device 36. In some embodiments, the optical fibers 30 may each have as few as one sensing section 32. In some such embodiments, the location and/or orientation of part of the optical fiber 30 is determined using another method. By way of example, the optical fiber may be fixed relative to another component that is visually tracked (e.g., the outer ring tracker 308).

The shape sensing capabilities of the optical fibers 30 provide a relative location of each point along the length of the optical fiber 30. In order to track the absolute location of each point along the length of the optical fiber 30, the optical fiber 30 may be located in a working coordinate system. The working coordinate system may be any type of three-dimensional coordinate system (e.g., a Cartesian coordinate system, a polar coordinate system, etc.). It may be advantageous to locate the origin at a specific point of interest (e.g., at the center of a robotic instrument, such as the surgical robot 212, at the fiber base 50, etc.), however any origin and orientation of the working coordinate system may be selected. The working coordinate system may be defined in relation to the surgical environment (i.e., the room in which a surgical procedure takes place) or in relation to an object within the surgical environment. Accordingly, the working coordinate system may move relative to the surgical environment if the object around which the working coordinate system is defined moves relative to the surgical environment.

Figure 5:
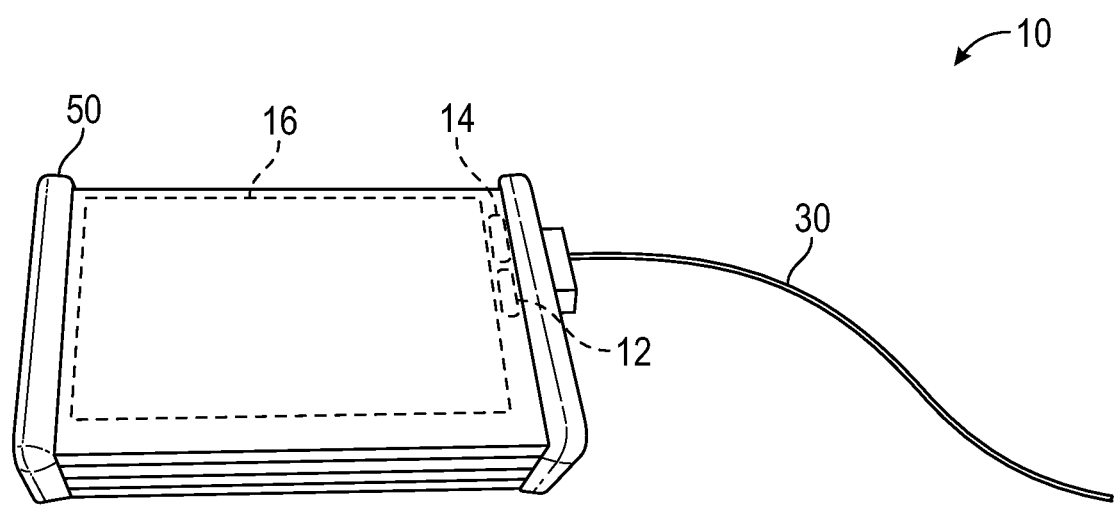
FIG. 5 provides a perspective view of a fiber optic tracking system.

To locate the optical fibers 30 in the working coordinate system, a pose (i.e., the location and the orientation) of each optical fiber 30 may be determined. According to an exemplary embodiment shown in FIG. 5, the light source 12, the sensing unit 14, and the controller 16 are contained within a fiber base 50. In this embodiment, a portion of each of the optical fibers 30 has a fixed location and orientation relative to the fiber base 50 near where each optical fiber 30 meets the fiber base 50. If a pose of the fiber base 50 in the working coordinate system and a shape of the optical fiber 30 are known, then the pose of each optical fiber 30 can be determined. In some embodiments, the pose of the fiber base 50 is determined by fixing it relative to another component, the pose of which in the working coordinate system has been previously determined. In some embodiments, this component is tracked using other means (e.g., the vision tracking system 60). In other embodiments, this component has a fixed location relative to the coordinate system. By way of example, if the fiber optic tracking system 10 is employed in an operating room, the fiber base 50 may be fixed to a component that is permanently fixed to the operating room floor.

In other embodiments, such as the embodiment illustrated in FIG. 1, the fiber optic tracking system 10 tracks the fiber base 50 or another object to determine its pose. This may be accomplished using a vision tracking system 60 shown in FIGS. 1 and 2. The vision tracking system 60 includes a camera 62 operatively coupled to the controller 16. The camera 62 may be located such that the field of view of the camera 62 is minimally obscured. By way of example, the camera 62 may be located on a ceiling or on an elevated stand. In some embodiments, the vision tracking system 60 uses vision recognition (e.g., of shapes, of colors, of reflective surfaces) to determine the pose of the fiber base 50 or another object in the working coordinate system. In some embodiments, the vision tracking system 60 recognizes the fiber base 50 directly. In other embodiments, one or more visual trackers 64 are attached to the fiber base 50 in predetermined locations. The visual trackers 64 include easily identifiable vision targets (e.g., retroreflective targets, targets with specific patterns, etc.). These vision targets may allow the controller 16 to determine both the location and the orientation of the visual trackers 64. By way of example, the vision targets may include a set of three retroreflective spheres in a known, fixed orientation relative to the vision tracker. Upon determining the location and/or pose of the one or more visual trackers 64, the controller 16 may determine the pose of the fiber base 50 using previously known information regarding the relative poses of the trackers 64 and the fiber base 50.

Figure 6:
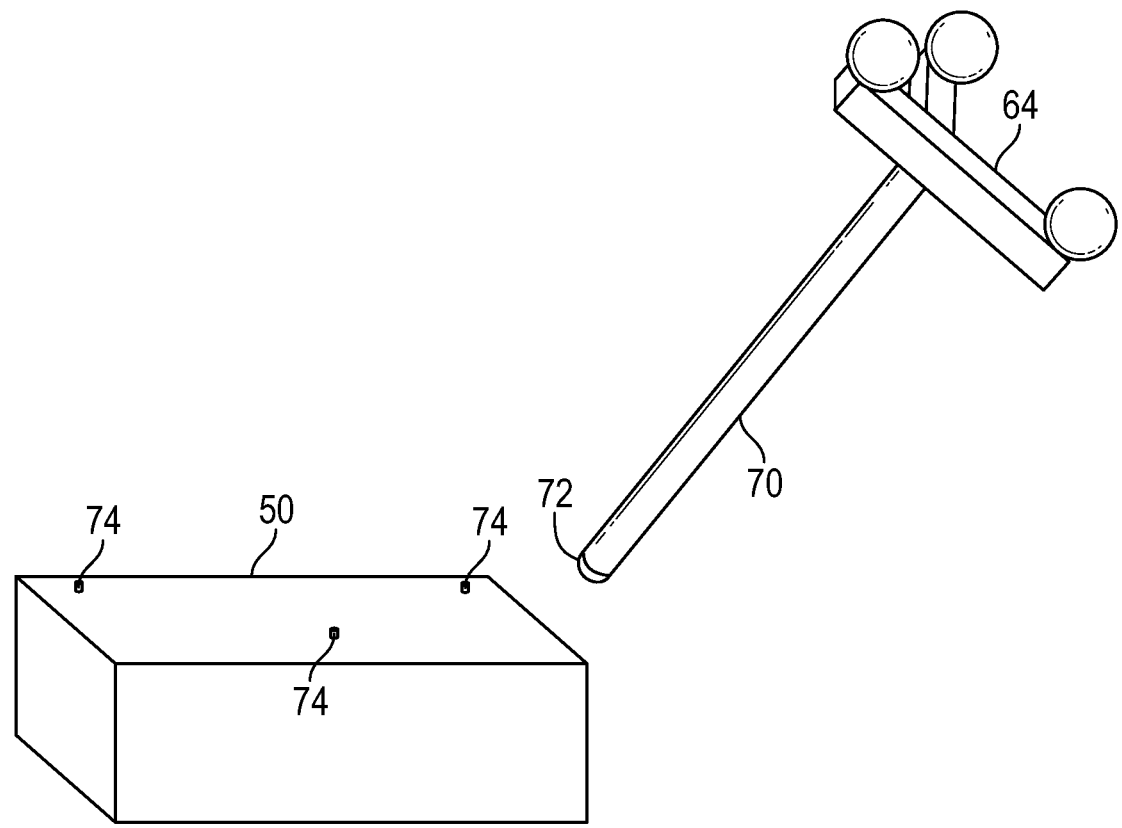
FIG. 6 illustrates an embodiment wherein a tracked probe is utilized to determine a pose of an object in a working coordinate system.

Referring to FIG. 6, the fiber optic tracking system 10 according to an exemplary embodiment may alternatively locate the fiber base 50 or another object in the working coordinate system using a tracked probe 70. The tracked probe 70 may be used to determine the location and/or contour (e.g., shape) of surfaces in the working coordinate system by contacting the surfaces. The tracked probe 70 may include a blunt end 72 used to contact the various surfaces. In other embodiments, the end 72 is sharp or otherwise shaped. The location of the end 72 is tracked as it is moved across a surface in order to determine the locations at which the end 72 contacts the surface. By way of example, one or more visual trackers 64 may be attached to a portion of the tracked probe 70 in order to determine a pose of the tracked probe 70, from which the location of the end 72 can be determined using previously known information regarding the relative 6D poses of the end 72 and the visual trackers 64. In other embodiments, the pose of the tracked probe 70 is otherwise determined. The tracked probe 70 may then be moved across one or more surfaces of the fiber base 50 to locate it in the working coordinate system. In some embodiments, the fiber base 50 includes one or more checkpoints 74. The checkpoints 74 may have a predefined shape that can be recognized by the controller 16. The checkpoints 74 may be placed in preset locations on the fiber base 50 such that, upon contacting the checkpoints 74 with the tracked probe 70, the pose of the fiber base 50 may be determined. By way of example, an operator may contact a checkpoint with the end 72 and indicate to the controller 16 that the checkpoint 74 is contacted. In other embodiments, another conventional tracking system may be used to determine the pose of the fiber base 50.

In one exemplary embodiment of the fiber optic tracking system 10, the working coordinate system is defined relative to the fiber base 50. A first optical fiber 30 runs from the fiber base 50 to a first object (e.g., the surgical robot 212). A second optical fiber runs from the fiber base 50 to a second object (e.g., hard tissue 100). Once the poses of both objects are known relative to the fiber base 50, the pose of first object relative to the second object can be calculated. Accordingly, the pose of an object relative to the surgical environment does not necessarily need to be determined.

Hereinafter, the fiber optic tracking system 10 is used to determine the shape, size, and/or pose of soft tissue (e.g., soft tissue 112), hard tissue (e.g., hard tissue 100), and features (e.g., incisions, holes, protrusions, etc.) thereof. As shown in the exemplary embodiments of FIGS. 7A-7D, the optical fibers 30 may be coupled (e.g., directly or indirectly) to a surface of the tissue or may extend partially inside of the tissue. An anchoring mechanism 80 may be used to prevent relative motion (e.g., a change in location or a change in orientation) between certain portions of the optical fibers 30 (e.g., the fixed sensing points 120, a section of the optical fiber 30) and the tissue. In some embodiments, the optical fibers 30 are coupled directly to the surface of the tissue using the anchoring mechanism 80. The anchoring mechanism 80 may include staples, sutures, screws, tacks, pins, tape, barbs, or other mechanisms, and may be made from metal, plastic, some form of resorbable material, or another material. Each optical fiber 30 may be held at multiple points along its length by multiple anchoring mechanisms 80. Alternatively, each optical fiber 30 may be held at just a single point along its length by one anchoring mechanism 80.

Figure 7A:
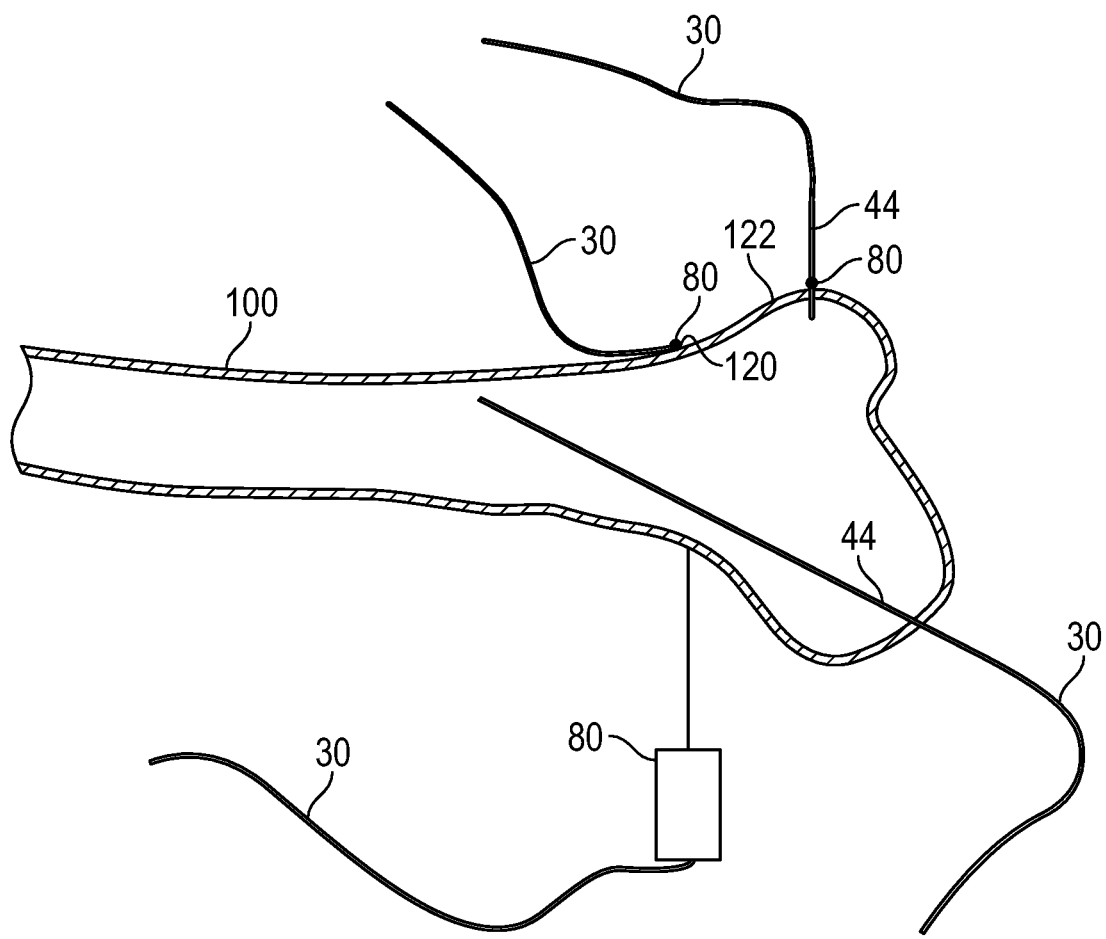
FIG. 7A provides a cross sectional view of an exemplary rigid object with a number of optical fibers attached, in accordance with certain disclosed embodiments.
Figure 7B:
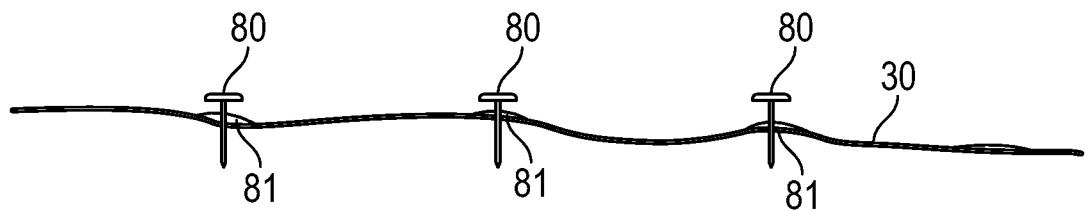
FIGS. 7B-7D provide perspective views of optical fibers including anchoring mechanisms, in accordance with certain disclosed embodiments.
Figure 7C:
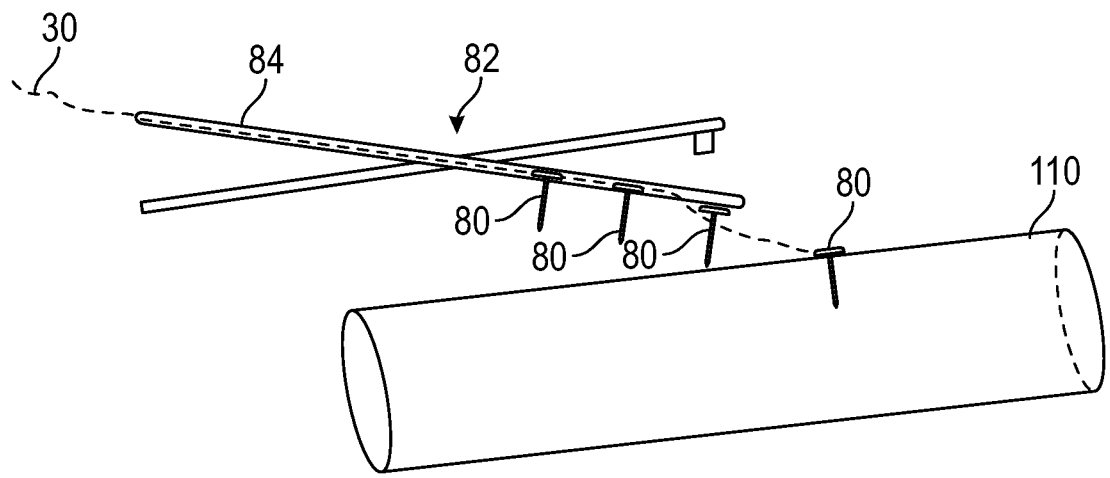
Figure 7D:
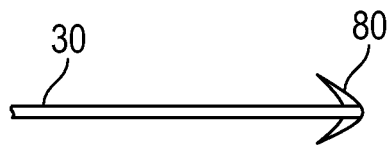

As shown in FIGS. 7B and 7C, the anchoring mechanism 80 is a tack configured to be pressed into tissue (e.g., with a tool similar to a stapler). In this embodiment, the optical fiber 30 is coupled to the anchoring mechanisms 80 such that they are fixed relative to one another at points along the length of the optical fiber 30. By way of example, the optical fiber 30 may include a number of loops of material (e.g., plastic) that are fixed (e.g., formed as an integral part of the protective outer layer 43) at regular intervals along the length of the optical fiber 30. These loops may each define an aperture 81 configured to receive an anchoring mechanism 80. The optical fiber 30 may be of sufficient strength that the anchoring mechanisms 80 may be removed from the tissue by applying a tensile force to the optical fiber 30. Referring to FIG. 7D, an optical fiber 30 includes a barb extending therefrom configured as an anchoring mechanism 80.

In some embodiments, such as the embodiment shown in FIG. 7B, the anchoring mechanism 80 is configured to penetrate or attach to the surface of tissue (e.g., bone, soft tissue, etc.) to couple the optical fiber 30 to the tissue. When anchoring an optical fiber 30 to bone, the anchoring mechanism 80 may couple to the outer surface of the bone (e.g., using adhesive), may extend into an outer layer of the bone, or may extend into the inter-medullary canal of the bone. In some embodiments, the anchoring mechanism 80 imparts a force on the optical fiber 30 to hold the optical fiber 30 directly against tissue. Alternatively, the optical fiber 30 may be indirectly coupled to the tissue using the anchoring mechanism 80, as shown in a portion of FIG. 7A. The optical fibers 30 may be coupled to a screw, pin, standoff, or other member, which in turn is coupled directly to the tissue. Alternatively, the optical fiber 30 may be coupled to material adjacent the tissue such as the muscle or cartilage adjacent a bone. In some embodiments, the optical fibers 30 include a rigid portion 44 that is configured to extend at least partially inside the tissue. By way of example, the rigid portion 44 may extend partially inside of an inter-medullary canal of a bone. The rigid portion 44 may be straight to facilitate penetration through the inner-medullary canal. A straight rigid portion 44 can be aligned with a bone to provide further information regarding the orientation of the bone. In some embodiments, an aperture is created (e.g., by drilling, using a needle) in the tissue, and the rigid portion 44 or a flexible portion of the optical fiber 30 is inserted into the tissue. In this case, the optical fiber 30 may be held in place by the anchoring mechanism 80, by coupling to material adjacent the tissue, by the portion of the optical fiber 30 that enters into the tissue being shaped to engage the hole into which it enters, or by some other means. The rigid portion 44 may be straight, curved, or otherwise shaped.

The system 10 may include one or more tools 82 used in the process of attaching the optical fibers 30. The tool 82 may be configured to at least one of pierce hard or soft tissue, grasp an optical fiber 30, insert an optical fiber 30 into tissue, couple an anchoring mechanism 80 to tissue and/or the optical fiber 30, and remove an optical fiber 30 and/or anchoring mechanism 80 from tissue. Referring to the embodiment shown in FIG. 7C, the tool 82 is configured to press anchoring mechanisms 80, shown as tacks, into tissue (e.g., hard tissue). The tool 82 may hold the tacks in place until they are attached to the tissue. As shown, a handle 84 of the tool 82 is squeezed, storing energy (e.g., in a spring) until the energy is released, impacting the tack into the tissue.

Figure 8A:
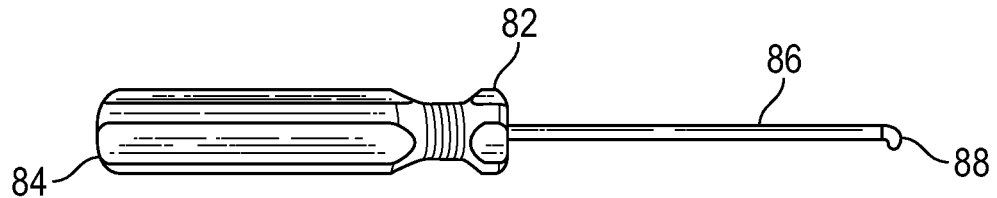
FIGS. 8A and 8B provide perspective views of a tool used in the attachment process of an optical fiber, in accordance with certain disclosed embodiments.
Figure 8B:
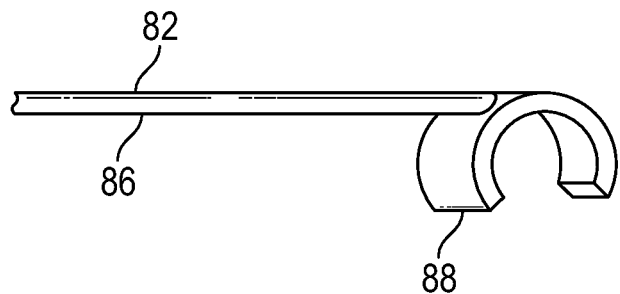

Referring to FIGS. 8A and 8B, the tool 82 is shown according to an alternative embodiment. The tool 82 includes a handle 84, a shaft 86 that may be made from a flexible material, and a tip 88 forming a hollow shape. The tool 82 may be used with a prior-made incision. As shown, the tip 88 is annular and includes a slot that allows it to move over an optical fiber 30. Once over the optical fiber 30, the tip 88 may be moved along the length of the optical fiber 30 until it contacts, for example, a barbed anchoring mechanism 80 as depicted in FIG. 7D. In some embodiments, two similar tools 82, each with tips 88 of different sizes are used. When applying the anchoring mechanism 80, a tip 88 smaller than the barbs is used to push the barbs into tissue. When removing the anchoring mechanism 80, a tip 88 larger than the barbs can be slid past the barbs and used to remove the barbs. By way of example, the tool 82 may be used to pull on the optical fiber 30 at a point beyond the barb. By way of another example, the tool 82 may be moved beyond the barb and used to pull back on the barb to remove it. In situations where the tool 82 is used to insert an anchoring mechanism 80 through soft tissue towards hard tissue, shaft 86 may be made from a flexible material to allow the shaft 86 to bend when contact is made with the hard tissue, allowing the optical fiber 30 to slide along the bone to reach a final insertion point.

Figure 9:
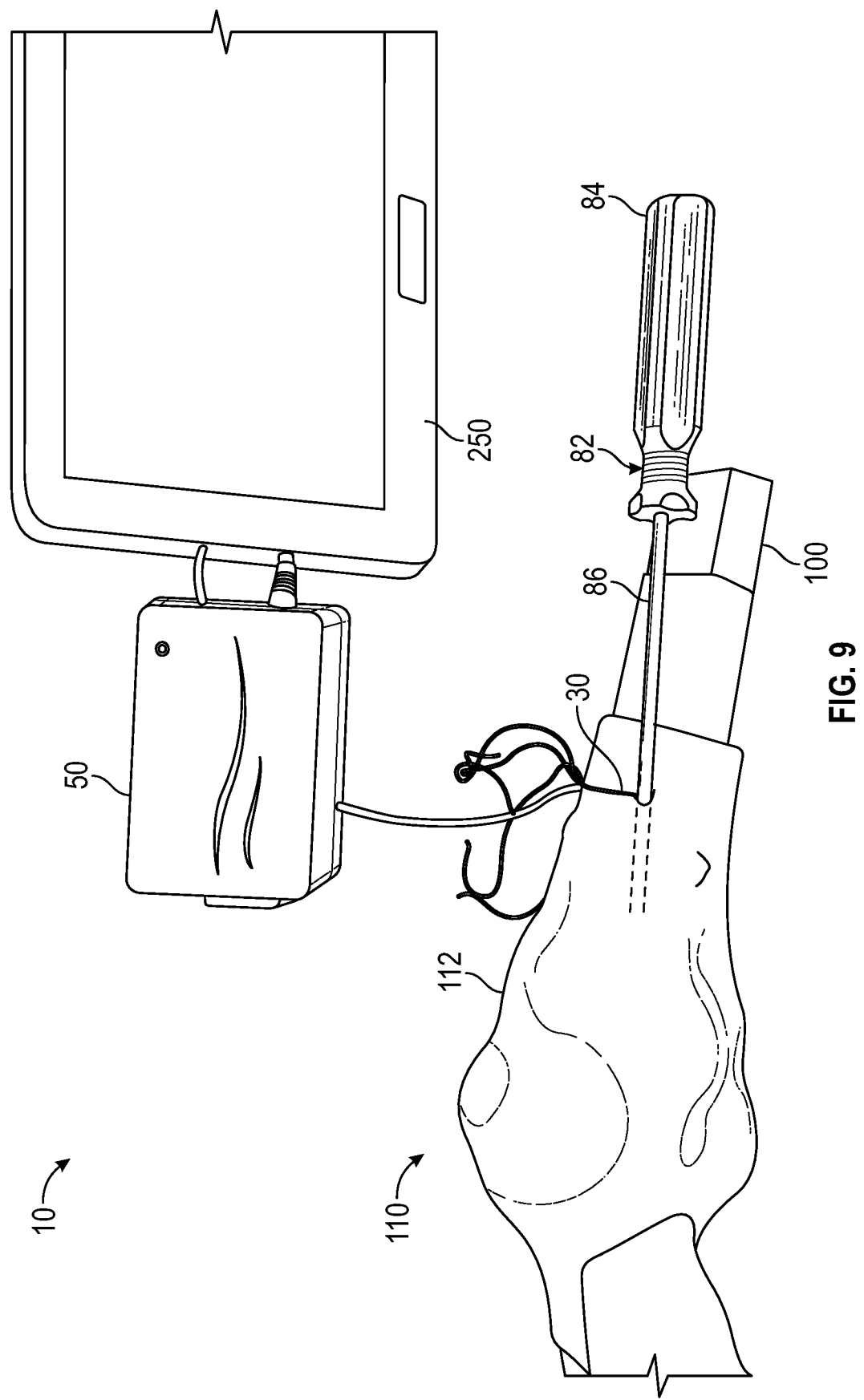
FIGS. 9-14 provide perspective views of a fiber optic tracking system.
Figure 10:
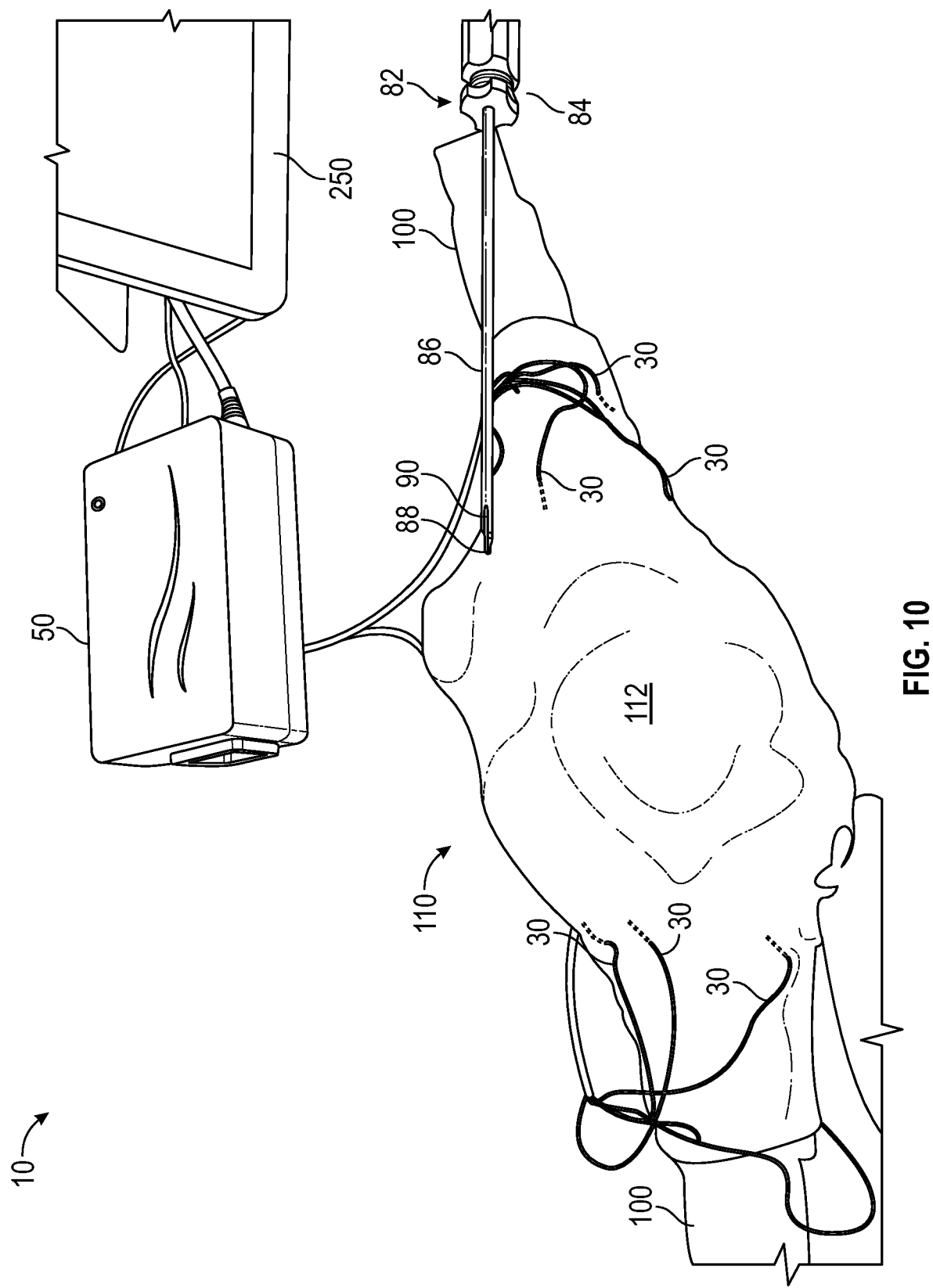

Referring to FIGS. 9 and 10, the tool 82 is shown according to another alternative embodiment, wherein the tool 82 is inserted through an incision in soft tissue surrounding hard tissue. The tool 82 may include a handle 84, a shaft 86, and a tip 88. In some embodiments, a small incision is made using known techniques (e.g., piercing with a needle, etc.), and the tool 82 is inserted into the small incision. In other embodiments, the tip 88 of the tool 82 is sharpened to facilitate insertion into the soft tissue, forming an incision as the tool 82 is inserted. The tool 82 may be configured to hold the optical fiber 30 in place relative to the tool 82 during the process of insertion (e.g., by placing the optical fiber in a groove 90). The groove 90 may be tapered and/or textured to effectively hold the optical fiber 30 without any actuating parts. The tool 82 may be configured to release the optical fiber 30 upon removal of the tool 82 from the soft tissue. The tool 82 may be configured to attach the optical fiber 30 to the hard tissue requiring only a small incision in the soft tissue to access the hard tissue, facilitating the tool 82 being minimally invasive.

In some embodiments, the tool 82 is configured to apply the anchoring mechanism 80 to the tissue. By way of example, the tool 82 may include a mechanism for driving a staple into hard tissue. The tool 82 may additionally be configured to drive a visual tracker 64 or a checkpoint 74 into tissue to facilitate location tracking. In some embodiments, the pose of the tool 82 is tracked in the working coordinate system (e.g., using a visual tracker 64 or by attachment to an optical fiber 30). The controller 16 may use the pose of the tool 82 to identify a location in the working coordinate system where the optical fiber 30, visual tracker 64, or checkpoint 74 is coupled to the tissue. The tool 82 may be powered (e.g., pneumatically, hydraulically, electrically, etc.), may operate using energy provided by an operator (e.g., by striking the tool 82, by loading a spring, etc.), or may be unpowered.

In some embodiments, the system 10 includes multiple tools 82, each performing a different function. By way of example, a first tool 82 may guide the optical fiber 30 into an incision, and a second tool 82 may apply the anchoring mechanism 80. In some embodiments, there is no soft tissue surrounding the hard tissue or the soft tissue is cut away prior to attachment of the optical fibers 30. By way of example, the soft tissue surrounding the hard tissue may be separated by an incision such that the hard tissue is not obstructed by the soft tissue. In some such embodiments, the tool 82 is still used to apply the anchoring mechanism 80 to the tissue and/or the optical fiber 30. In some embodiments where an operator has a direct line of sight to the tissue where the optical fiber 30 will be anchored, the tool 82 may be a standard medical driver able to insert a screw, tack, staple, or other anchoring mechanism 80. In other embodiments, the optical fiber 30 is otherwise coupled to the tissue (e.g., applying tape by hand).

Referring to FIGS. 9-14, the fiber optic tracking system 10 according to an exemplary embodiment is shown configured to determine a pose of a rigid object, shown as hard tissue 100, in the working coordinate system. As shown in FIGS. 9-14, the rigid object is hard tissue 100, specifically bone, however the fiber optic tracking system 10 may be used to detect the pose of any rigid object (e.g., a surgical instrument, a tooth, etc.) or soft tissue. In some embodiments, one or more optical fibers 30 are used to track hard tissue 100, and a visual tracker 64, the tracked probe 70, a checkpoint 74, and/or any other methods described herein may be used to initially determine the pose of the hard tissue 100 relative to the optical fiber 30. In some embodiments, the fiber optic tracking system 10 uses at least one optical fiber 30 attached (e.g., directly or indirectly) to the hard tissue 100 at at least two non-colinear points to determine the pose of the hard tissue 100. In another embodiment, the fiber optic tracking system 10 utilizes multiple optical fibers 30, each attached (e.g., directly or indirectly) to the hard tissue 100 at at least one point, when determining the pose of the hard tissue 100.

By way of a first example, the system 10 may include three optical fibers 30, each coupled to the hard tissue 100 or another rigid object such that a fixed sensing point 120 (e.g., as shown in FIG. 7A) along the length of each fiber 30 is fixed (i.e., has a fixed location) relative to the hard tissue 100. If the locations of three or more fixed sensing points 120 in the working coordinate system are determined, and the locations of the three or more fixed sensing points 120 relative to the hard tissue 100 are determined, then the pose of the hard tissue 100 in the working coordinate system can be determined. Alternatively, the system 10 may include one or more optical fibers 30 that are fixed relative to the hard tissue 100 at more than one fixed sensing point 120. By way of example, the system 10 may include one optical fiber 30 that is fixed relative to the hard tissue 100 at two fixed sensing points 120 and another optical fiber 30 that is fixed relative to the hard tissue 100 at one fixed sensing point 120. Alternatively, fewer than three fixed sensing points 120 may be used to determine the pose of the hard tissue 100 if the fixed sensing points 120 are fixed relative to the hard tissue 100 and the one or more optical fibers 30 associated with the fixed sensing points 120 each have a fixed orientation relative to the hard tissue 100 at the fixed sensing points 120. In such an embodiment, the locations of the fixed sensing points 120 and the orientations of the optical fibers 30 at the fixed sensing points 120 in the working coordinate system may be determined, and the locations of the fixed sensing points 120 and the orientations of the optical fibers 30 at the fixed sensing points 120 relative to the hard tissue 100 may be determined, thereby facilitating the determination of the pose of the hard tissue 100 in the working coordinate system. In a first example, the optical fibers 30 may be assumed to be tangent to the hard tissue 100 at the fixed sensing points 120. In another example, a section of an optical fiber 30 may be held against a surface of the hard tissue 100 such that the optical fiber 30 conforms to a contour of a surface of the hard tissue 100. More optical fibers 30 and/or fixed sensing points 120 may be utilized to increase the accuracy of the determined pose.

In FIGS. 9-14, a surrogate knee model 110 is shown. The model 110 includes a number of pieces of hard tissue 100, shown as surrogate bones, surrounded by material, shown as soft tissue 112. It should be understood that the fiber optic tacking approach described herein may be employed on the hard tissue of a human or animal or on another rigid object. Referring to FIG. 9, an optical fiber 30 is shown partway through the process of insertion into the soft tissue 112 of the model 110.

Figure 11:
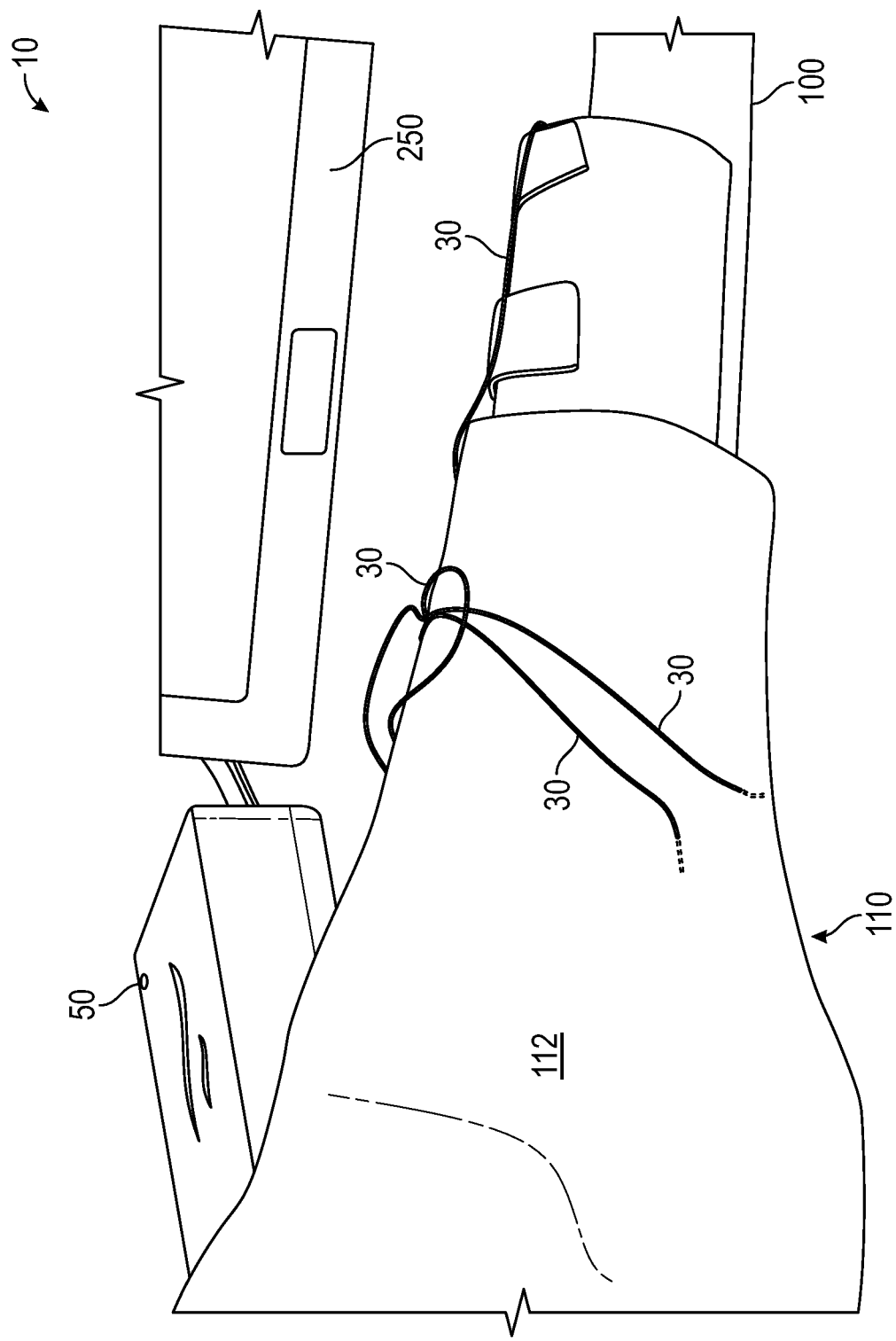
Figure 12:
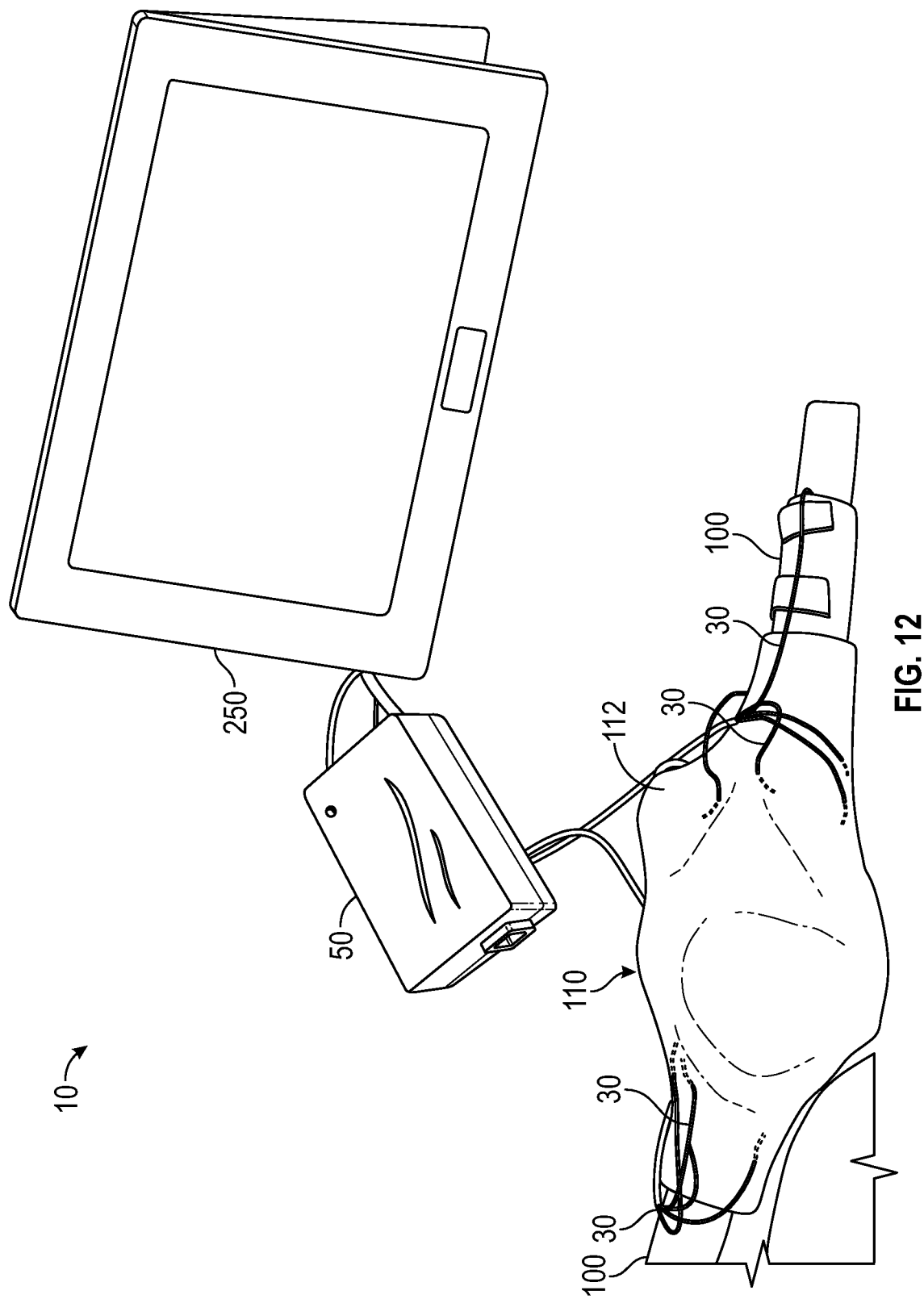

Referring to FIGS. 9-14, the optical fibers 30 are shown attached to the hard tissue 100. In some embodiments, the fiber optic tracking system 10 is configured to track more than one piece of hard tissue 100 simultaneously. This may be accomplished using additional optical fibers 30 or by attaching a single optical fiber 30 to multiple pieces of hard tissue 100. As shown in FIG. 11, at least three optical fibers 30 are attached to the hard tissue 100 such that at least one fixed sensing point 120 (shown in FIG. 7A) along the length of each optical fiber 30 is in a fixed location relative to the hard tissue 100 (i.e., has a fixed relationship to the hard tissue 100, is fixed relative to the hard tissue 100). Once the optical fibers 30 are attached, locations of the points 120 in the working coordinate system can be determined.

The shape and pose of each optical fiber 30 in the working coordinate system may be determined using the modified optical signals as described above. The controller 16 may be configured to determine the locations of the fixed sensing points 120 in the working coordinate system by determining the locations of the fixed sensing points 120 along the length of each optical fiber 30. In one such instance, the optical fibers 30 are attached such that the fixed sensing points 120 are each located at an endpoint of their respective optical fibers 30. By way of example, the anchoring mechanism 80 may hold the endpoint of the optical fiber 30 in contact with an exterior surface of the hard tissue 100. In another instance, the locations of the fixed sensing points 120 along the length of the optical fiber 30 may be predetermined and set at a specified distance along the length of the optical fiber 30. By way of example, the optical fiber 30 may be sutured to the hard tissue 100 such that the fixed sensing point 120 is located at a specified distance along the length of the optical fiber 30. The predetermined location of the point 120 along the length of the optical fiber 30 may be visibly marked (e.g., by a change in color of the outer layers of the optical fiber 30) to facilitate accurate attachment by an operator. By way of another example, the optical fiber 30 may be manufactured and/or assembled such that the anchoring mechanism 80 has a fixed relationship to a point along the length of the optical fiber 30, such as shown in FIG. 7B.

In some embodiments, the controller 16 may be configured to determine the locations of the fixed sensing points 120 using information from the tracked probe 70. By way of example, the operator may contact the end 72 of the tracked probe 70 to the various fixed sensing points 120 to register their locations in the working coordinate system. In some embodiments, the pose of the tool 82 is tracked while attaching the optical fiber 30 to the hard tissue as described above (e.g., by tracking an optical fiber attached to the tool 82, using a visual tracking system, etc.). The pose of the tool 82 may be used to determine the locations of the fixed sensing points 120. By way of example, if the fixed sensing point 120 is located between a staple and the hard tissue 100, the pose of the tool 82 while attaching the staple may be used to determine the location of the fixed sensing point 120. As shown in FIG. 9, the tool 82 inserts the optical fibers 30 through an incision in soft tissue 112 surrounding the hard tissue 100. In some embodiments, the anchoring mechanism 80 is configured to couple the optical fiber 30 to the hard tissue 100 beneath the outer surface of the soft tissue 112 such that a fixed sensing point 120 is located beneath the outer surface of the soft tissue 112 (e.g., between an outer surface of the soft tissue 112 and the hard tissue 100). By way of example, the anchoring mechanism 80 may be a suture that couples the optical fiber 30 directly to an outer surface of the hard tissue 100 such that a fixed sensing point 120 is provided directly on an outer surface of the hard tissue 100. Accordingly, tracking the location of the fixed sensing point 120 using the pose of the tool 82 may be beneficial, as the fixed sensing point 120 may be obscured by the soft tissue 112.

In some embodiments, the controller 16 is configured to determine the locations of the fixed sensing points 120 along the length of each optical fiber 30 by moving the one or more optical fibers 30. The controller 16 may be configured to analyze the relative movements of each of the optical fibers 30 to determine which points along the length of each optical fiber 30 are stationary relative to points along the lengths of the other optical fibers 30 or relative to other points on the same optical fiber 30. The points that do not move relative to points on the other optical fibers 30 or relative to points on the same optical fiber 30 may be considered fixed sensing points 120. Alternatively, the optical fiber 30 may be configured to sense the force imparted on the optical fiber 30 at different points along the length of the optical fiber 30 (e.g., using measured strains at points along the length of the optical fiber 30). The force sensing may be done using an additional core 40 or an additional optical fiber 30 that runs along the same path as optical fiber 30 used to determine the pose of an object. In embodiments where the anchoring mechanism 80 imparts a force on the optical fiber 30 (e.g., where the anchoring mechanism 80 is a staple that holds the optical fiber 30 against a bone), the optical fiber 30 may experience a sharp increase in bending deflection and/or force on the optical fiber 30 near the anchoring mechanism 80. The bending deflection and/or force at different points along the length of the optical fiber 30 may be used to determine the location of the fixed sensing points 120. By way of example, the rate of change of bending deflection and/or force applied to the optical fiber 30 along the length of the may be analyzed to locate the fixed sensing points 120. Areas of the optical fiber 30 where this rate of change has a high magnitude may be fixed sensing points 120.

To determine the pose of the hard tissue 100 in the working coordinate system, the controller 16 may be configured to determine a shape of a surface 122 (e.g., the surface 122 shown in FIG. 7A) of the hard tissue 100 and the locations of the fixed sensing points 120 relative to the surface 122. The controller 16 then registers the shape of the surface 122 to a three-dimensional model of the hard tissue 100. Knowing the locations of the fixed sensing points 120 relative to the hard tissue 100, the controller 16 is configured to determine the pose of the hard tissue 100. By way of example, a three-dimensional model of a bone may be generated prior to an operation using conventional scanning techniques (e.g., computerized tomography (CT) scanning, magnetic resonance imaging (MM), etc.). The controller 16 is configured to register the pose of the surface 122 to the three-dimensional model (e.g., by matching contours of the surface 122 to a section of the three-dimensional model) such that the pose of the entire hard tissue 100 can be determined using the pose of the surface 122 in the working coordinate system.

To determine the shape and pose of the surface 122 relative to the fixed sensing points 120, the controller 16 determines a shape and a pose of the surface 122 in the working coordinate system, and compares this to the locations of the fixed sensing points 120 in the working coordinate system. The shape and the pose of the surface 122 may be determined using a variety of methods. By way of example, the shape and the pose of the surface 122 may be determined by running the tracked probe 70 over the surface 122 of the hard tissue 100. The controller 16 may configured to record the locations in the working coordinate system of points on the surface 122 that are contacted by tracked probe 70. The controller may then calculate the shape and pose of the portion of the surface 122 contacted by the tracked probe 70.

In some embodiments, the tracked probe 70 incorporates a force sensor (e.g., a strain gauge, an optical fiber 30 configured to measure force or strain, etc.) near the end 72 to determine when the end 72 contacts the surface 122. When the end 72 is contacting the surface 122, the tracked probe 70 experiences an axial compressive force, causing a deflection (i.e., a strain) of the tracked probe 70. An optical fiber 30 may be configured such that it is axially fixed to the tracked probe 70 at two fixed points, where at least one sensing section 32 is disposed between the two fixed points. These sensing sections 32 experience the same strain as the tracked probe 70 between the two fixed points. Using the material properties of the tracked probe 70 and the strain measured by these sensing sections, the compressive force on the tracked probe 70 is determined. In some embodiments, the temperature near the tracked probe 70 is measured (e.g., with a thermocouple, with a thermistor, etc.), and the measured strain is compensated for temperature. In some such embodiments, a second optical fiber 30 is included near where this strain is measured. The second optical fiber 30 is axially fixed at two points such that it remains a constant length. However, only one of the points is fixed relative to the tracked probe 70. Accordingly, this second optical fiber 30 experiences no change in strain when a force is applied to the tracked probe 70. Because the strain measurements measured by sensing sections 32 on the second optical fiber 30 vary with temperature but not axial force, they can be used to determine the temperature surrounding the tracked probe 70.

By way of another example, the pose of the surface 122 may be determined using conventional imaging techniques to capture a three-dimensional model of the hard tissue 100 and/or the surroundings of the hard tissue 100. In this example, registration of the surface 122 to the three-dimensional model may not be necessary, as the pose of the three-dimensional model may be provided by the imaging. Intraoperative imaging (i.e., imaging performed during surgery) may be used as it can provide pose information after the optical fibers 30 have been attached. The imaging may additionally locate the optical fibers 30 relative to the hard tissue 100. By way of yet another example, if an incision surrounding the hard tissue 100 is large enough, video recognition may be used to identify the surface 122. A camera, such as the camera 62 or another camera, may be configured to capture an image of the surface 122. The controller 16 may then match this image to a portion of the three-dimensional model.

Alternatively, in embodiments where a section of each optical fiber 30 is held against the surface 122, the shape and pose of each optical fiber 30 may be used to determine the contours and the pose of the surface 122. By way of example, this may be employed when two or more points within a section of each optical fiber 30 held against the surface 122 are attached directly to the surface 122 of the hard tissue 100 (e.g., such that the points are fixed sensing points 120). If the optical fiber 30 is attached such that the length of optical fiber 30 contacting the surface 122 is not mobile relative to the hard tissue 100 (e.g., the optical fiber is taut along this length), then the optical fiber 30 follows a contour of the surface 122, and one or more of these contours may be matched to the three-dimensional model of the hard tissue 100. Depending upon the length of the contour followed by the optical fiber 30, multiple of these contours may be used to more accurately match to the three-dimensional model.

Figure 13:
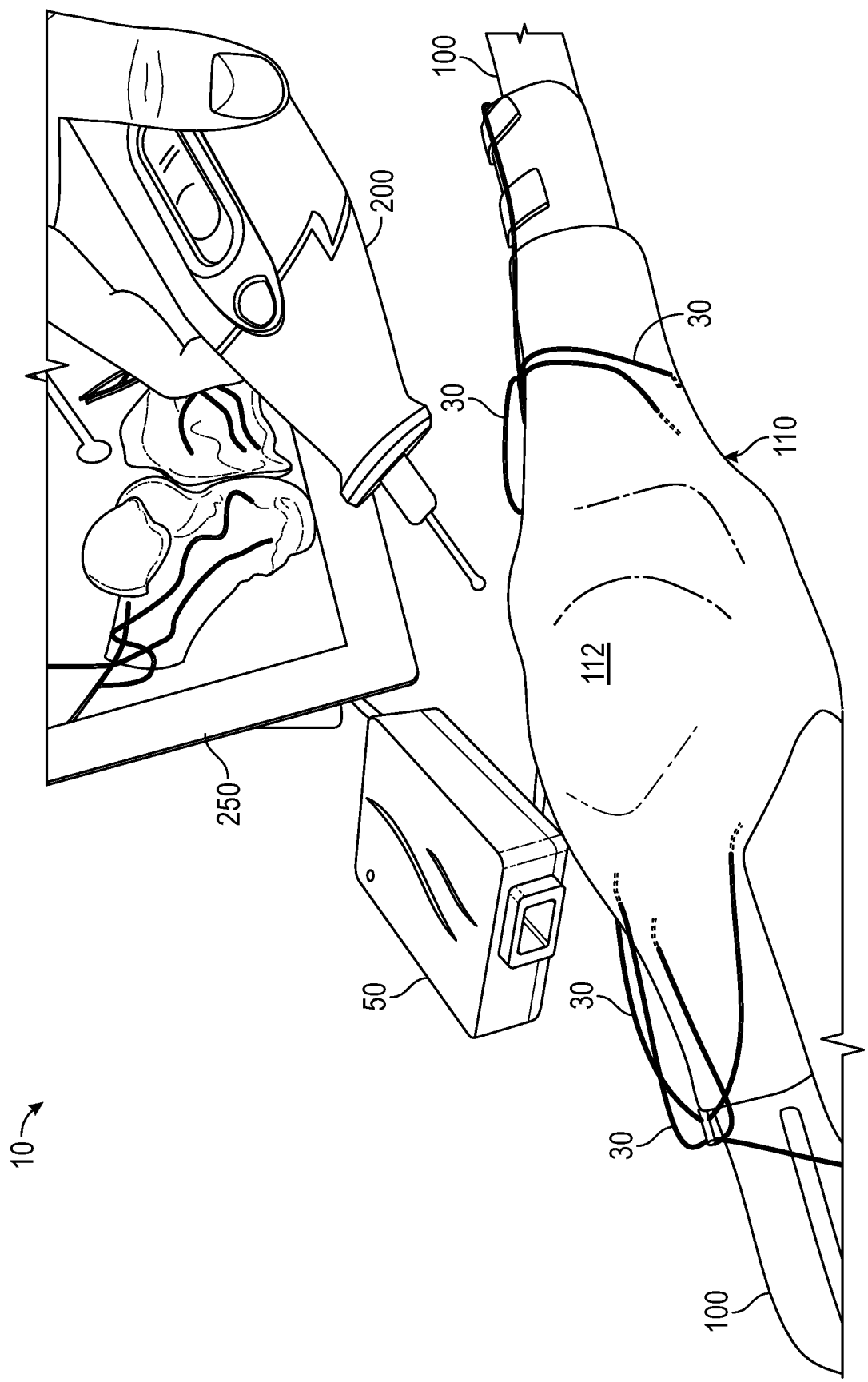
Figure 14:
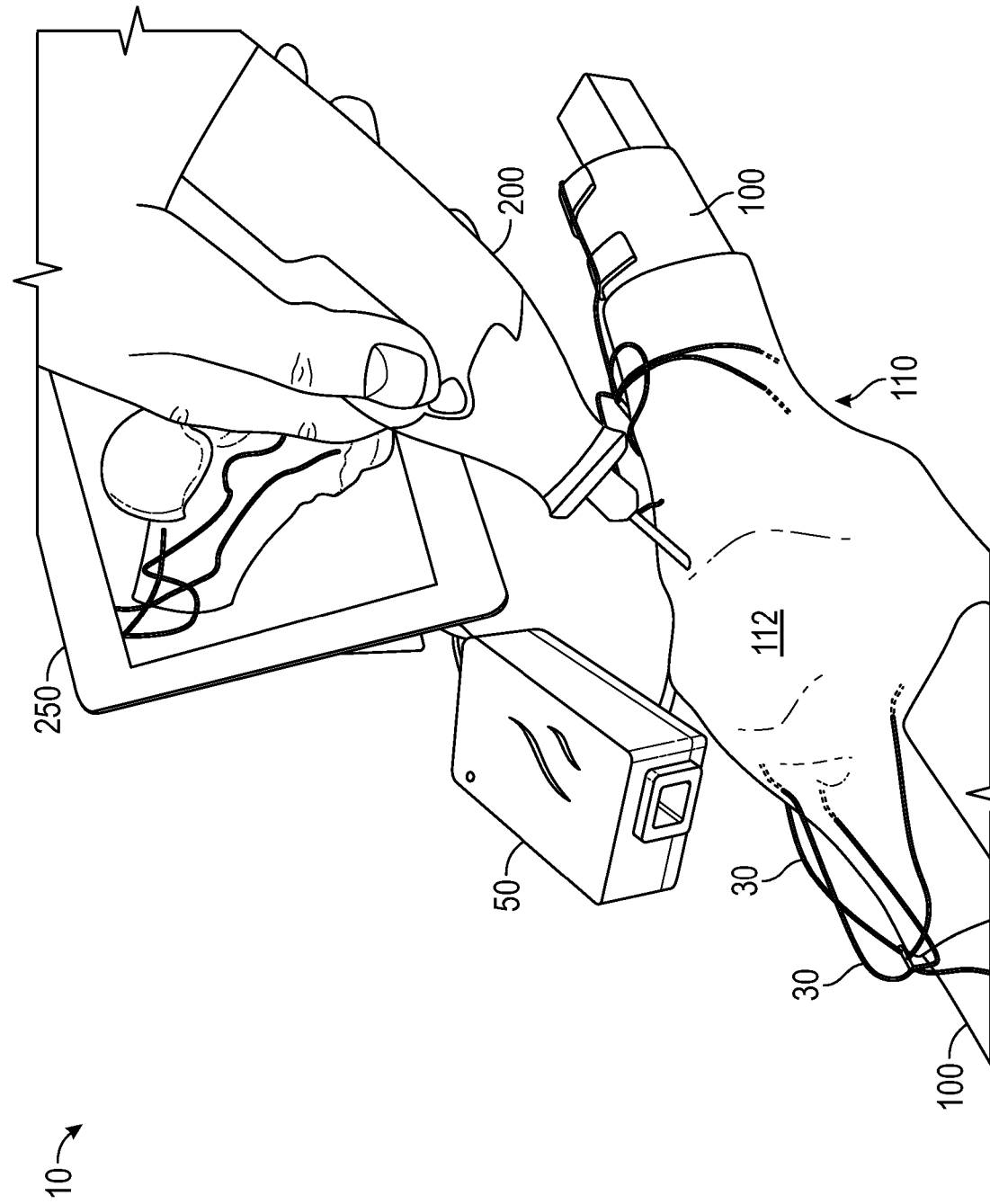

Referring to FIGS. 13 and 14, a surgical instrument 200, shown as a cutting tool, is used to perform a surgical operation according to an exemplary embodiment. The pose of the surgical instrument 200 in the working coordinate system may be determined using any conventional methods or any of the methods described herein (e.g., using the vision tracking system 60, by tracking one or more optical fibers 30 attached to the surgical instrument 200, etc.). The pose of the surgical instrument 200 and the poses of the one or more pieces of hard tissue 100 may be sent to a computer-assisted surgical system 210. The computer-assisted surgical system 210 may include one or more pieces of tracked or navigated surgical equipment (e.g., cutting tools, surgical robots, etc.), shown as surgical robots 212, controlled using information supplied by the fiber optic tracking system 10. The surgical robot 212 may guide or control the surgical instrument 200 or any other surgical instruments during surgery. In some embodiments, parts of the fiber optic tracking system 10, such as the tracked probe 70 or the tool 82, are controlled by the surgical robot 212.

Figure 15:
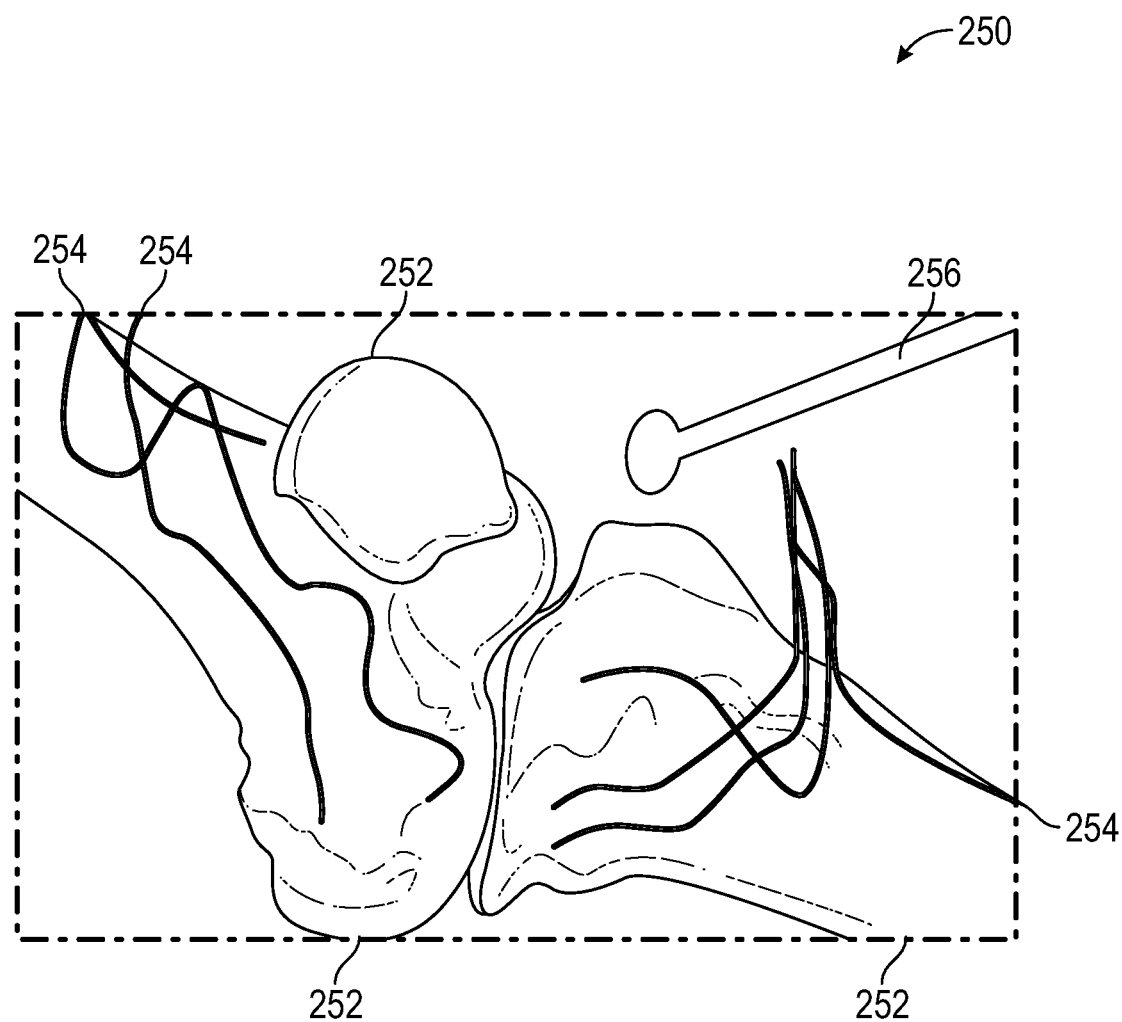
FIG. 15 illustrates an exemplary screen shot associated with a display of a fiber optic tracking system, in accordance with certain disclosed embodiments.

As shown in FIGS. 13 and 14 the fiber optic tracking system may include a graphical user interface or display 250 operatively coupled to the controller 16. In some embodiments, the display 250 is part of the computer-assisted surgical system 210. As shown in FIGS. 13 and 14, the display 250 displays or indicates a relative pose of one or more of the pieces of hard tissue 100, the optical fibers 30, the tracked probe 70, and the surgical instrument 200. In other embodiments, the display 250 additionally or alternatively displays the soft tissue 112, other tissue, and/or another item. FIG. 15 shows an exemplary screenshot of the display 250. This screenshot shows three-dimensional hard tissue models 252 of the pieces of hard tissue 100, three-dimensional optical fiber models 254 of the optical fibers, and a three-dimensional surgical instrument model 256 of the surgical instrument 200. Having the display 250 show the relative poses of the various objects assists an operator in accurately navigating during a surgery, as many of these objects would normally be obscured during an operation (e.g., by soft tissue 112).

Figure 16:
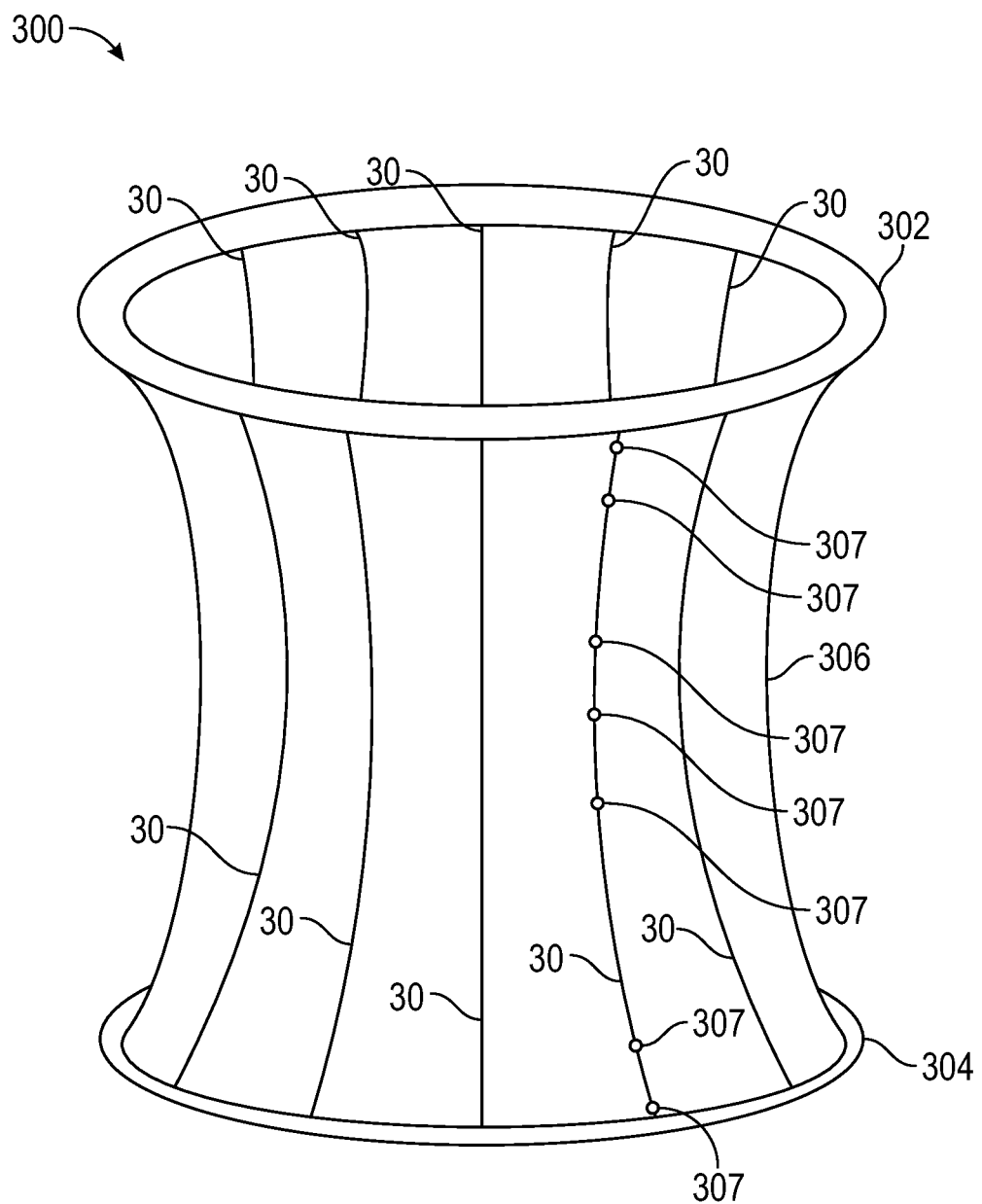
FIG. 16 provides a perspective view of a surgical port, in accordance with certain disclosed embodiments.
Figure 17:
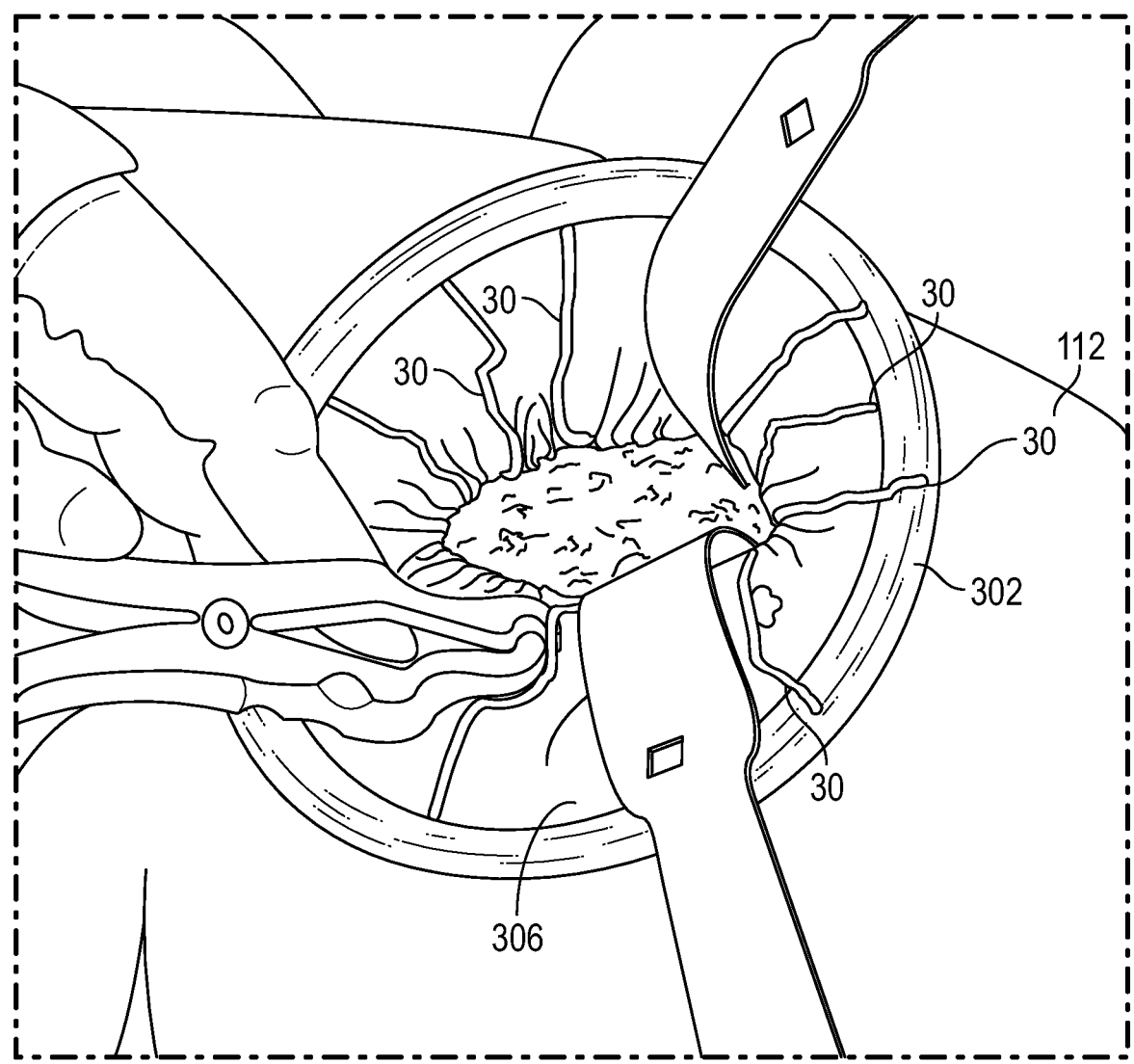
FIGS. 17 and 18 illustrate embodiments where a surgical port is used to retract a wound.
Figure 18:
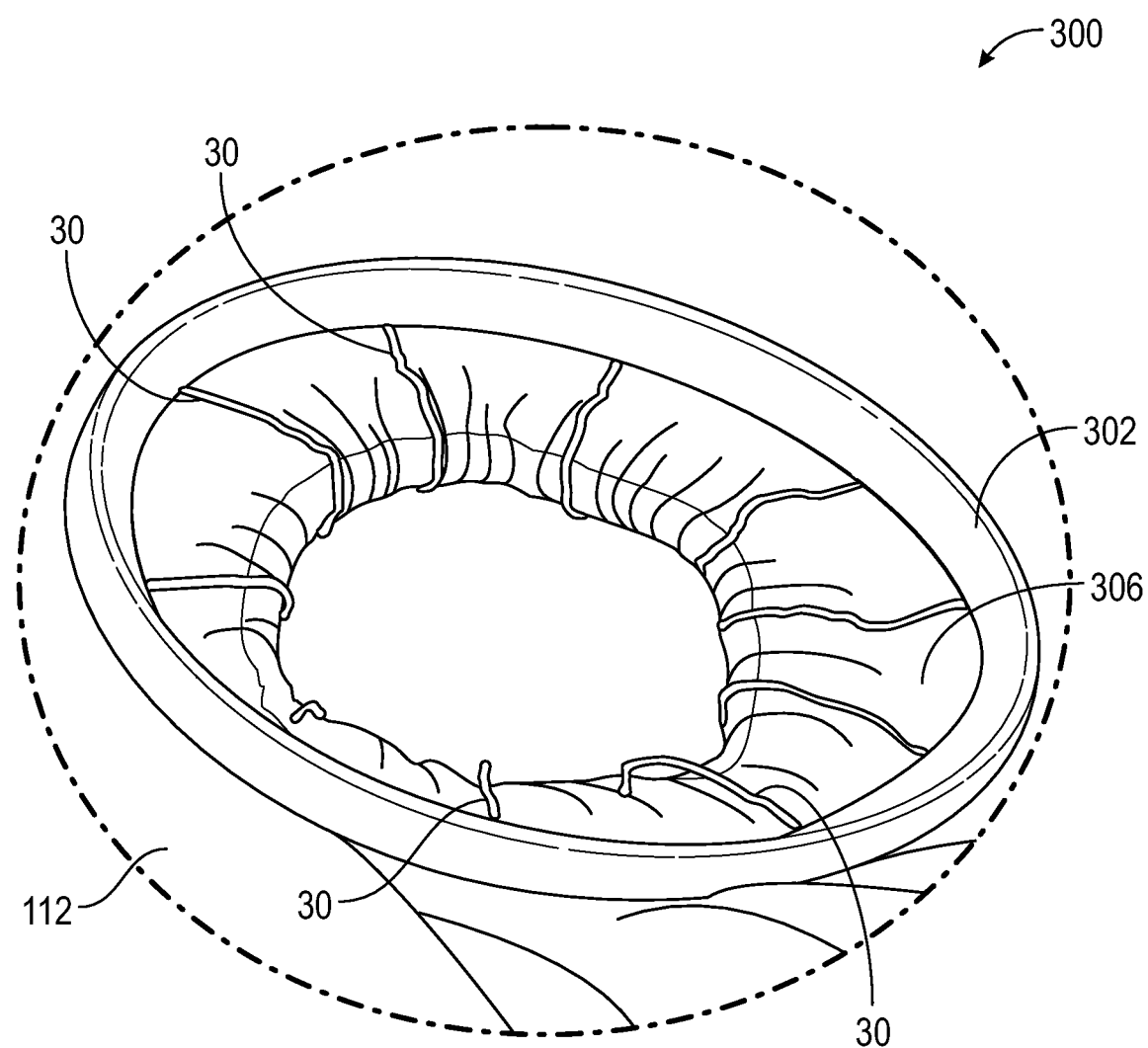

Referring to FIG. 16, a surgical port 300 used to sense a shape and/or a pose of an incision in soft tissue 112 of a body (e.g., a human body, a body of an animal, etc.) is shown according to an exemplary embodiment. The surgical port 300 is configured to be inserted within (e.g., completely within, partially within, etc.) the incision. The surgical port 300 includes an outer protrusion, shown as outer ring 302, an inner protrusion, shown as inner ring 304, and a flexible wall 306 coupling the outer ring 302 to the inner ring 304 and forming a central aperture. The flexible wall 306 is coupled to the inner ring 304 and the outer ring 302 as shown in FIG. 16 such that it forms a continuous (e.g., elliptical, circular, rectangular, etc.) shape. The inner ring 304 and the outer ring 302 may be flexible or rigid. FIGS. 17 and 18 show the surgical port 300 in place during a surgery. The surgical port 300 may be used to retract the incision to facilitate access to the interior of a body through the incision. The flexible wall 306 covers and contacts the incision and protects the surrounding soft tissue 112. The inner ring 304 may be inserted into the incision by, for example, bending it over upon itself. Once the inner ring 304 is located inside of the incision, the outer ring 302 may be rolled such that the flexible wall 306 is retracted onto the outer ring 302. This applies tension to the flexible wall 306, conforming the flexible wall 306 to the shape of the incision and causing the incision to retract (i.e., increase in size). Once fully retracted, at least a portion of the outer ring 302 contacts the soft tissue 112 surrounding the incision, resting upon an outer surface of the body as shown in FIGS. 17 and 18. In other embodiments, the outer ring 302 and inner ring 304 may be otherwise shaped.

As shown in FIGS. 16-18, one or more optical fibers 30 of the fiber optic tracking system 10 are integrated into the surgical port 300 according to an exemplary embodiment. In some embodiments, the fiber optic tracking system 10 includes the surgical port 300 and does not track the hard tissue 100. As shown in FIG. 16, the optical fibers 30 are radially distributed around the flexible wall 306, conform to the contours of the flexible wall 306, and extend away from the surgical port 300 to connect to the fiber base 50. Sections of the optical fibers 30 contacting the flexible wall 306 are flexible, allowing them to deform to conform to the contours of the flexible wall 306 if the flexible wall 306 deforms. The portions of the optical fibers 30 extending towards the fiber base 50 are omitted from FIGS. 16-18 for clarity, although it should be understood that the optical fibers 30 extend away from the incision and past the outer ring 302. The optical fibers 30 are coupled to the surgical port 300 such that one or more fixed sensing points 307 along the lengths of each of the optical fibers 30 have a fixed relationship to the surgical port 300. Specifically, one or more of the fixed sensing points 307 may have a fixed relationship to the outer ring 302, the inner ring 304, and/or the flexible wall 306. FIG. 16 shows exemplary locations of fixed sensing points 307, although it should be understood that the fixed sensing points 307 may be included on each optical fiber 30, and that there may be a different number (e.g., 1, 2, 100, 1000, etc.) of fixed sensing points 307 on each optical fiber 30. The optical fiber 30 may be coupled to the flexible wall 306 such that the optical fiber has a number of fixed sensing points 307 fixed relative to the flexible wall 306. The optical fibers 30 may be coupled to an interior surface or an exterior surface of the flexible wall 306 or located inside of the flexible wall 306 itself. In some embodiments, the optical fibers 30 are permanently coupled to the flexible wall 306 (e.g., the flexible wall 306 is molded around the optical fibers 30). In other embodiments, the optical fibers 30 may be removable from the flexible wall 306 (e.g., adhered to an exterior surface of the flexible wall 306).

The fiber optic tracking system 10 may be configured to use the optical fibers 30 to determine a shape, size, and pose of the flexible wall 306. Because the flexible wall 306 contacts and conforms to the soft tissue 112 surrounding the incision, this information can be used to determine the shape, size, and pose of the incision. As the flexible wall 306 is retracted onto the outer ring 302, it conforms to the shape of the incision. The radially placed optical fibers 30 conform to the shape of the incision as well, each following a contour of the incision. As shown in FIGS. 16-18, the optical fibers 30 extend longitudinally along the surgical port 300. In other embodiments, the optical fibers 30 are angled relative to the longitudinal direction. By way of example, the optical fibers 30 may form a spiral shape along a surface of the flexible wall 306. Such an arrangement facilitates providing detailed information regarding the shape of the incision using a relatively small number of optical fibers 30.

The controller 16 may determine a shape and a pose of each of the optical fibers 30 in the working coordinate system. The controller 16 may then be configured to locate the fixed sensing points 307 along the length of each optical fiber 30. Once the fixed sensing points 307 are located along an optical fiber, their locations in the working coordinate system are known. In some embodiments, a section of an optical fiber 30 may be fixed to the flexible wall 306 such that any point along the portion is a fixed sensing point 307. In other embodiments, each optical fiber 30 is fixed relative to the flexible wall 306 at a number of fixed sensing points 307 separate from one another. In some embodiments, the locations of the fixed sensing points 307 along the length of each optical fiber 30 are predetermined and stored in the memory device 36. By way of example, the optical fibers 30 may be bonded to the flexible wall 306 in a precise location when manufacturing the surgical port 300. In some embodiments, the locations of the fixed sensing points 307 along the length of each optical fiber 30 are determined by contacting the portion of the optical fiber 30 that is fixed to the flexible wall 306 with the tracked probe 70. In other embodiments, other methods of locating the fixed sensing points 307 are utilized.

The controller 16 may be configured to determine a curve that best fits the fixed sensing points 307 corresponding to each optical fiber 30. This curve may be substantially similar to the shape of the portion of the optical fiber 30 coupled to the flexible wall 306. The controller 16 may then calculate a shape that forms a best fit to all of the curves. This shape may be substantially similar to the shape of the flexible wall 306 and the incision. The controller 16 may then match the locations of the fixed sensing points 307 on the determined shape to the locations of the fixed sensing points 307 in the working coordinate system to locate the shape in the working coordinate system. Additionally, the locations of the fixed sensing points 307 may be used to determine the size of this shape. Because the flexible wall 306 conforms to the shape of the incision, the pose and size of this shape may be used to determine a pose, a size, and a shape of the incision. The addition of more fixed sensing points 307 may increase accuracy when determining the shape of the incision, especially if the soft tissue 112 surrounding the incision experiences a non-uniform load (e.g., a singular hook-shaped retractor pulling on the incision).

As shown in FIG. 18, the flexible wall 306 wraps around the soft tissue 112 at the incision, such that if a surgical instrument, such as the surgical instrument 200, stays within the central aperture, the surgical instrument will not contact the soft tissue 112 surrounding the incision. This prevents accidental damage to the soft tissue 112 that might otherwise occur without the shape and pose information provided by the optical fibers 30. Additionally, the flexible wall 306 allows the surgical port 300 to conform to outside forces, such as the wound retractors shown in FIG. 18, while still providing shape and pose information.

Figure 19:
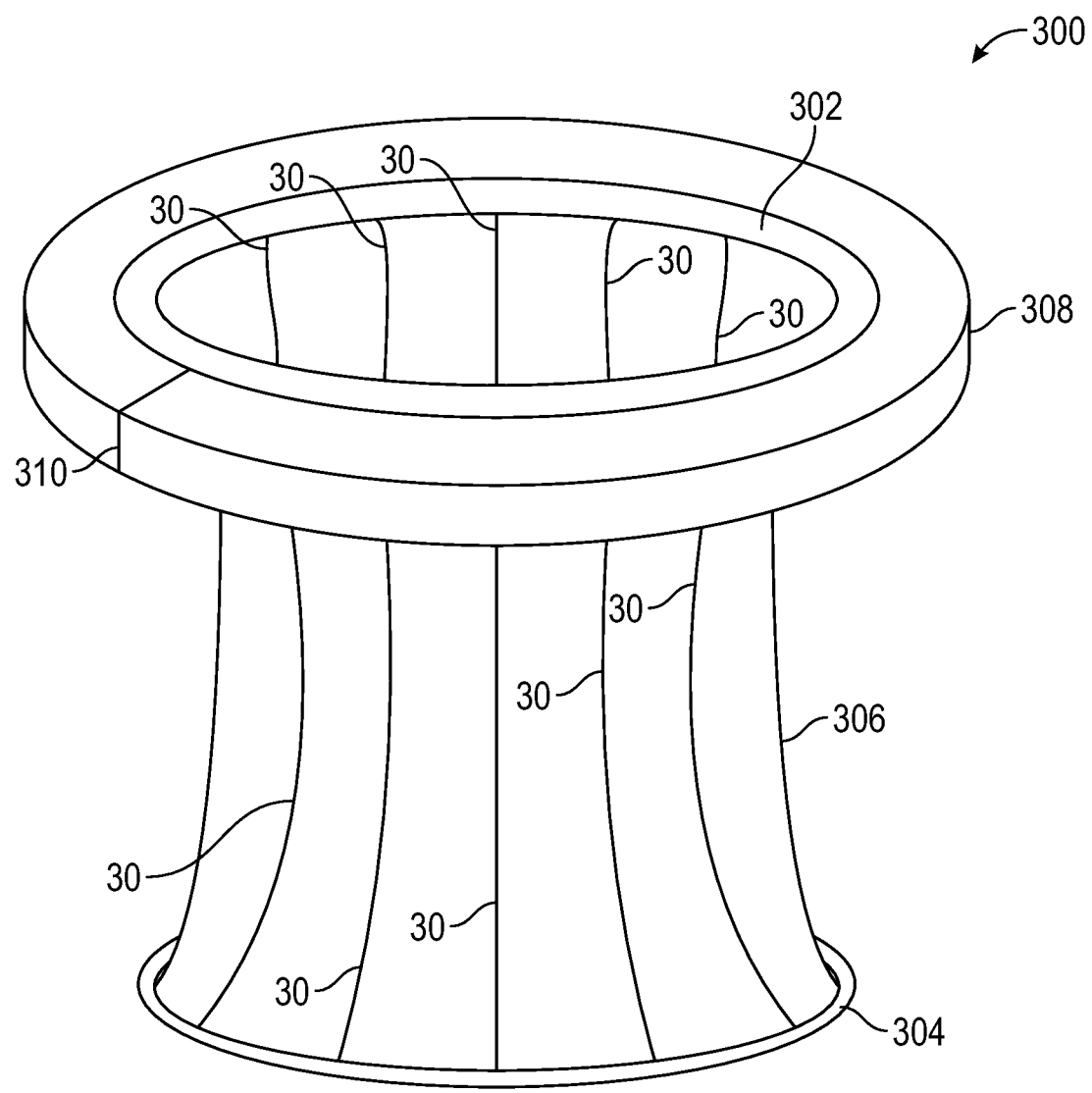
FIG. 19 provides a perspective view of a surgical port, in accordance with certain disclosed embodiments.

Referring to FIG. 19, in some embodiments, a tracker, shown as outer ring tracker 308, is removably or selectively coupled to the outer ring 302. The outer ring tracker 308 may be attached to the outer ring 302 after the outer ring 302 is rolled to retract the flexible wall 306. As shown in FIG. 19, the outer ring tracker 308 is annular and couples to the outer ring 302 by applying a circumferential clamping force. To produce the clamping force, a compressive force is exerted on a slot 310 in the outer ring tracker 308 (e.g., by tightening a screw extending perpendicular to the slot 310), decreasing an inner diameter of the outer ring tracker 308. In other embodiments, the outer ring tracker 308 is otherwise held onto the outer ring 302. By way of example, the outer ring tracker 308 may include a clamp that extends on either side of the flexible wall 306 and applies a clamping force on the outer ring 302. The outer ring tracker 308 is coupled to the outer ring 302 such that relative motion between the outer ring tracker 308 and the outer ring 302 is prevented.

The outer ring tracker 308 includes a tracking mechanism for determining a pose of the outer ring tracker 308 in the working coordinate system. Because the outer ring tracker 308 has a fixed relationship to the outer ring 302, the pose of the outer ring tracker 308 may be used to determine a pose of the outer ring 302. Because the outer ring 302 contacts an outer surface of the body and the flexible wall 306 forms a continuous shape coupled to the outer ring 302, the pose of the outer ring tracker 308 may be used to determine a pose of an entry into the incision in the working coordinate system. By way of example, the entry may be considered the inner diameter of the outer ring 302.

The controller 16 may be configured to register the pose of the outer ring tracker 308 relative to the optical fibers 30 to determine where along the length of the optical fibers 30 the entry is located. The information regarding the pose of the entry may be used to determine which points along the length of each optical fiber 30 are fixed sensing points 307 coupled to the flexible wall 306. By way of example, the controller 16 may consider all of the points along each optical fiber 30 that are located beyond the entry to be fixed sensing points 307, and use these fixed sensing points 307 when determining the shape of the incision. By way of another example, the controller 16 may consider all of the points along each optical fiber 30 that are located a certain distance beyond the entry to be fixed sensing points 307. By way of yet another example, the controller 16 may determine a pose of the inner ring 304 in the working coordinate system and consider the points along the lengths of the optical fibers 30 that are located between the outer ring 302 and the inner ring 304 to be fixed sensing points 307. One or more optical fibers 30 may be used to determine a pose of the inner ring 304 in the working coordinate system (e.g., by attaching an optical fiber 30 to a circumference of the inner ring 304).

In the embodiment shown in FIG. 19, a portion of the surface of the outer ring tracker 308 facing away from the soft tissue 112 is retroreflective, and the vision tracking system 60 is used to determine its pose in the working coordinate system. In other embodiments, one or more visual trackers 64 or checkpoints 74 are coupled to the outer ring tracker 308 and used to determine the pose of the outer ring tracker 308. In yet other embodiments, one or more optical fibers 30 are coupled to the outer ring tracker 308 and used to determine the pose of the outer ring tracker 308. In yet other embodiments, the controller 16 determines the pose of the outer ring tracker 308 using another method. Given a fixed relationship between the outer ring tracker 308 and the entry (e.g., because the outer ring tracker 308 is coupled to the outer ring 302), the controller 16 may use the pose of the outer ring tracker 308 to determine a pose of the entry.

In some embodiments, the outer ring tracker 308 is omitted. The tracked probe 70 may be run along the surface of the outer ring 302 to determine the shape and pose of the entry. Alternatively, one or more optical fibers 30 may be fixed to the surgical port 300 at one or more fixed sensing points 307 whose locations relative to the surgical port 300 are known. After determining the locations of these fixed sensing points 307 in the working coordinate system, the shape and pose of the surgical port 300 are known. If the pose of the entry relative to the rest of the surgical port 300 is known, then the pose of the entry in the working coordinate system is known. The addition of more fixed sensing points 307 further increases the accuracy of this method. Once the shape of the incision and the pose of the entry have been determined, the shape and pose of the incision are known.

In some embodiments, the controller 16 provides the shape and the pose of the incision determined using the surgical port 300 to the computer-assisted surgical system 210. The computer-assisted surgical system 210 may use this information when determining a pathway for the surgical robot 212 to follow when performing an operation. Without the fiber optic tracking system 10, the computer-assisted surgical system 210 would lack information regarding the shape and pose of the incision, and could cause the surgical instrument 200 to come into contact with and damage the soft tissue 112 surrounding the incision. The information provided by the fiber optic tracking system 10 allows the computer-assisted surgical system 210 to ensure that the surgical instrument 200 used during the operation (e.g., a cutting tool) stays within the central aperture of the surgical port 300, preventing contact between the surgical instrument 200 and the soft tissue 112.

In some embodiments, the fiber optic tracking system 10 tracks the hard tissue 100 and does not track the incision. In other embodiments, the fiber optic tracking system 10 tracks the incision and does not track the hard tissue 100. In yet other embodiments, the fiber optic tracking system 10 tracks the hard tissue 100 and the incision. In some such embodiments, the fiber optic tracking system 10 includes separate optical fibers 30 for tracking the hard tissue 100 and the incision. In other such embodiments, one or more optical fibers 30 are used to track both the incision and the hard tissue 100. By way of example, an optical fiber 30 may be coupled to the flexible wall 306 and extend inside the body through the incision to be coupled to a surface of the hard tissue 100. Accordingly, each optical fiber 30 in such an arrangement would have one or more fixed sensing points 120 and one or more fixed sensing points 307.

In some embodiments, the display 250 displays to a user a shape and a pose of the incision (e.g., including the pose of the entry) or the surgical port 300. In some such embodiments, the display 250 additionally displays the relative poses of one or more of the pieces of hard tissue 100, the optical fibers 30, the tracked probe 70, and the surgical instrument 200. Having the display 250 show the relative poses of the various objects relative to the incision assists an operator in accurately navigating during an operation. By way of example, the display may show the operator how close the surgical instrument 200 is to contact with the soft tissue 112.

In an alternative embodiment, optical fibers 30 are attached to or inserted into soft tissue 112 and used to track an incision or some other area of interest. One or more optical fibers 30 may be inserted into or attached to the soft tissue 112 using the tool 82 and an anchoring mechanism 80 or some other method or attached to the exterior of the soft tissue 112. The locations of the incisions and the points of attachment of the optical fibers 30 to the soft tissue 112 may be determined. By way of example, the tracked probe 70 may be moved across one or more of the areas of interest (e.g., an inner surface of the incision), any exposed points of contact between the optical fibers 30 and the soft tissue 112 (e.g., where the optical fiber 30 meets the exposed surface of the soft tissue 112), and the exposed soft tissue 112. Alternatively, the tool 82 may be tracked when inserting or attaching the optical fibers 30 to locate the optical fibers 30. The relative poses of the optical fibers 30, the soft tissue 112, and the area of interest may be determined, and this may be used to track the area of interest based on the poses of the optical fibers 30. This information may be provided to a computer assisted surgical system 210 and/or a display 250.

Figure 20:
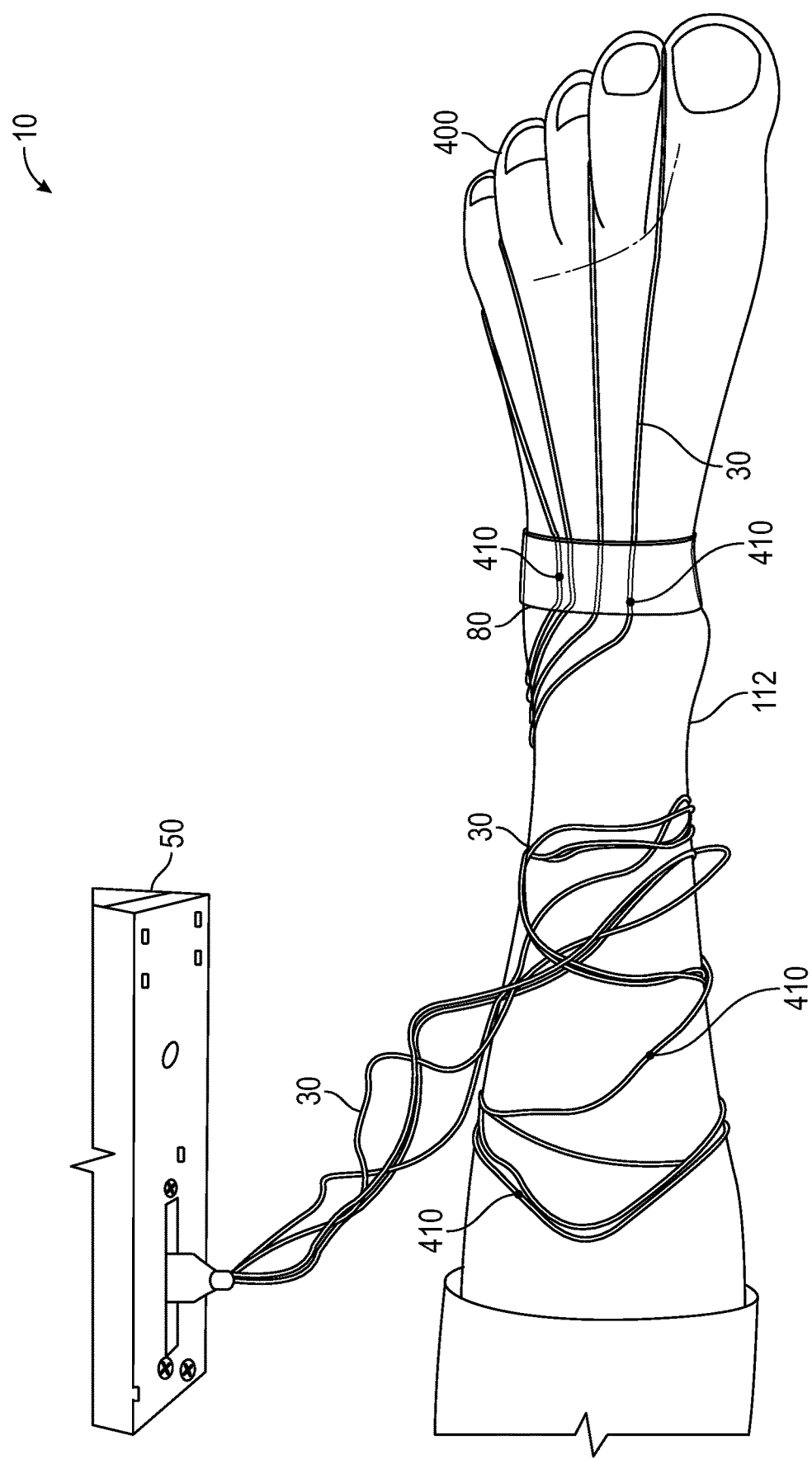
FIG. 20 provides a perspective view of an object outfitted with a number of optical fibers, in accordance with certain disclosed embodiments.

As shown in FIG. 20, the fiber optic tracking system 10 according to an exemplary embodiment can be used to determine the dimensions, shape, and/or pose of an object 400. As shown, the object 400 is soft tissue 112 (e.g., a human leg tracked at the exterior of the body), however a similar method may be used with hard tissue 100 or any other type of object 400. One or more optical fibers 30 may be wrapped around or otherwise held against an outer surface of the object 400, and the shapes and poses of the optical fibers 30 may be determined as discussed above. The optical fibers 30 may be held in place relative to the object 400 (e.g., using an anchoring mechanism 80 such as tape, by wrapping the optical fibers 30 tightly around the object 400, etc.) at a number of fixed sensing points 410. Sections of the optical fibers 30 may be held in place relative to the object 400 such that the shapes of those sections conform to contours of the outer surface of the object 400. The locations of the fixed sensing points 410 in these sections may be used to determine the overall shape, dimensions, and/or pose of the object 400. The optical fibers 30 may be placed in certain key locations (e.g., between toes), providing the location and/or pose of certain parts of the object 400 (e.g., toes, fingers, a heel, etc.). This may facilitate registration of the shape information from the optical fibers 30 to a model of the object 400. The overall shape and/or dimensions of the object 400 may be used in further operations for alignment with other devices or other purposes.

The foregoing descriptions have been presented for purposes of illustration and description. They are not exhaustive and do not limit the disclosed embodiments to the precise form disclosed. Modifications and variations are possible in light of the above teachings or may be acquired from practicing the disclosed embodiments. For example, the described implementation includes software, but the disclosed embodiments may be implemented as a combination of hardware and software or in firmware. Examples of hardware include computing or processing systems, including personal computers, servers, laptops, mainframes, microprocessors, and the like. Additionally, although disclosed aspects are described as being stored in a memory, one skilled in the art will appreciate that these aspects can also be stored on other types of computer-readable storage devices, such as secondary storage devices, like hard disks, floppy disks, a CD-ROM, USB media, DVD, or other forms of RAM or ROM.

It will be apparent to those skilled in the art that various modifications and variations can be made to the disclosed systems and associated methods for fiber optic tracking of hard and soft tissue. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A fiber optic tracking system, comprising: a surgical port comprising a flexible wall configured to be inserted into an incision; a light source; an optical fiber coupled to the surgical port and having a plurality of fixed sensing points located along a length of the optical fiber, wherein the plurality of fixed sensing points are positioned on and fixed relative to the flexible wall of the surgical port, and wherein the optical fiber: is configured to receive an optical signal from the light source; and includes a plurality of sensing sections arranged along the length of the optical fiber and configured to modify the optical signal received by the optical fiber in response to a deformation of the optical fiber; a sensing unit configured to receive a modified optical signal from the optical fiber; and a controller operatively coupled to the sensing unit and configured to determine locations in a working coordinate system of the fixed sensing points using the modified optical signal and to determine a shape of the incision using the locations of the fixed sensing points.

2. The fiber optic tracking system of claim 1, further comprising: a second optical fiber coupled to the surgical port and having a plurality of second fixed sensing points located along the length of the second optical, where in the plurality of second fixed sensing points are positioned on and fixed relative to the flexible wall, wherein the second optical fiber: is configured to receive a second optical signal from the light source; and includes a plurality of second sensing sections arranged along a length of the second optical fiber and configured to modify the second optical signal received by the second optical fiber in response to a deformation of the second optical fiber; wherein the controller is configured to determine the shape of the incision using the locations of the first fixed sensing points and the second fixed sensing points.

3. The fiber optic tracking system of claim 1, wherein the surgical port includes an outer protrusion coupled to the flexible wall, wherein the controller is configured to determine a pose of the outer protrusion in the working coordinate system, and wherein the controller is configured to determine a pose of an entry to the incision in the working coordinate system based on the pose of the outer protrusion.

4. The fiber optic tracking system of claim 3, further comprising a tracker selectively coupled to the outer protrusion, wherein the controller is configured to determine a pose of the tracker in the working coordinate system, and wherein the controller is configured to determine the pose of the outer protrusion based on the pose of the tracker.

5. The fiber optic tracking system of claim 3, further comprising a display operatively coupled to the controller, wherein the controller is configured to determine a pose of a surgical instrument within the working coordinate system, and wherein the display is configured to indicate to a user the pose of the entry relative to the pose of the surgical instrument.

6. The fiber optic tracking system of claim 1, wherein the optical fiber is configured to extend through the incision and couple to hard tissue such that an additional fixed sensing point along the length of the optical fiber is fixed relative to the hard tissue, and wherein the controller is configured to determine a location of the additional fixed sensing point within the working coordinate system.

7. The fiber optic tracking system of claim 1, wherein the optical fiber is arranged to conform to the incision when the flexible wall of the surgical port conforms to the incision.

8. The fiber optic tracking system of claim 1, wherein the plurality of fixed sensing points are spaced apart from one another.

9. The fiber optic tracking system of claim 8, wherein locations of the plurality of fixed sensing points along the one or more optical fibers is predetermined and stored in a memory device of the controller.

10. A method of tracking an incision, comprising: inserting a surgical port into the incision; providing a light source; coupling an optical fiber to the surgical port such that a plurality of fixed sensing points are located along a length of the optical fiber and are positioned on and fixed relative to a flexible wall of the surgical port, wherein the optical fiber: is configured to receive an optical signal from the light source; and includes a plurality of sensing sections arranged along the length the optical fiber and configured to modify the optical signal received by the optical fiber in response to a deformation of the optical fiber; receiving a modified optical signal from the optical fiber; and determining locations in a working coordinate system of the fixed sensing points based on the modified optical signal the method further comprising determining a shape of the incision using the locations of the fixed sensing points.

11. The method of claim 10, wherein the surgical port includes an outer protrusion coupled to the flexible wall, further comprising: determining a pose of the outer protrusion in the working coordinate system; and determining a pose of an entry to the incision in the working coordinate system using the pose of the outer protrusion.

12. The method of claim 11, further comprising: coupling a tracker to the outer protrusion; determining a pose of the tracker in the working coordinate system; and determining the pose of the outer protrusion based on the pose of the tracker.

13. The method of claim 10, further comprising: extending the optical fiber through the incision; coupling the optical fiber to hard tissue such that an additional fixed sensing point along the length of the optical fiber is fixed relative to the hard tissue; and
determining a location of the additional fixed sensing point within the working coordinate system.

14. The method of claim 10, further comprising determining a shape of the flexible wall based on the modified optical signal.

15. The method of claim 10, further comprising determining a shape of the incision based on the shape of the flexible wall.

16. A system for tracking an incision, comprising: an integrated device, comprising: an outer ring; an inner ring; a flexible wall extending from the outer ring to the inner ring and configured to define a shape of the incision when the flexible wall is positioned in the incision; one or more optical fibers integrated with the flexible wall and configured to conform to the shape of the flexible wall, the one or more optical fibers comprising a plurality of fixed sensing points positioned on and fixed relative to the flexible wall; and a controller configured to determine the shape of the incision and a pose of the incision based on data collected using the one or more optical fibers.

17. The system of claim 16, wherein the controller is configured to determine a size of the incision based on the data collected using the one or more optical fibers.

18. The system of claim 16, wherein the optical fiber further comprises an additional fixed sensing point fixed relative to the outer ring.

19. The system of claim 16, wherein the optical fiber further comprises an additional fixed sensing point fixed relative to the inner ring.

20. The fiber optic tracking system of claim 16, wherein the optical fiber further comprises a first additional fixed sensing point fixed relative to the outer ring and a second additional fixed sensing point fixed relative to the inner ring of the surgical port.

21. The fiber optic tracking system of claim 16, wherein the one or more optical fibers are formed in a spiral shape along a surface of the flexible wall.

* * * * *